(12) United States Patent
Burke et al.

(10) Patent No.: US 9,804,068 B2
(45) Date of Patent: Oct. 31, 2017

(54) PARTICLE SEPARATION AND CONCENTRATION USING SPIRAL INERTIAL FILTRATION

(71) Applicant: Canon U.S. Life Sciences, Inc., Rockville, MD (US)

(72) Inventors: Jeffrey M Burke, Rockville, MD (US); Ian M White, Rockville, MD (US)

(73) Assignee: University of Maryland, College Park, MD (US)

( * ) Notice: Subject to any disclaimer, the term of this patent is extended or adjusted under 35 U.S.C. 154(b) by 781 days.

(21) Appl. No.: 14/042,043

(22) Filed: Sep. 30, 2013

(65) Prior Publication Data

US 2014/0093867 A1    Apr. 3, 2014

Related U.S. Application Data

(60) Provisional application No. 61/707,878, filed on Sep. 8, 2012.

(51) Int. Cl.
*G01N 1/34*     (2006.01)
*G01N 1/40*     (2006.01)
(Continued)

(52) U.S. Cl.
CPC .......... *G01N 1/34* (2013.01); *B01D 21/0087* (2013.01); *B01D 21/2444* (2013.01);
(Continued)

(58) Field of Classification Search
CPC ...... G01N 1/34; G01N 1/4077; B01D 21/265; B01L 3/502776; B01L 3/502753;
(Continued)

(56) References Cited

U.S. PATENT DOCUMENTS 6,884,360 B2    4/2005  Chang
7,727,399 B2    6/2010  Leonard et al.
(Continued)

FOREIGN PATENT DOCUMENTS

EP    2 127 752 A2    12/2009
FR    2 918 900 A1    1/2009
WO    2011/109762 A1    9/2011

OTHER PUBLICATIONS

G.F. Carrier, et al., "Particle Transport in a Counter-flow," Combustion and Flame, 126:1630-1639 (2001).

*Primary Examiner* — David A Reifsnyder
(74) *Attorney, Agent, or Firm* — Rothwell, Figg, Ernst & Manbeck, P.C.

(57) ABSTRACT

A spiral inertial filtration device is capable of high-throughput (1 mL/min), high-purity particle separation while concentrating recovered target particles by more than an order of magnitude. Large fractions of sample fluid are removed from a microchannel without disruption of concentrated particle streams by taking advantage of particle focusing in inertial spiral microfluidics, which is achieved by balancing inertial lift forces and Dean drag forces. To enable the calculation of channel geometries in the device for specific concentration factors, an equivalent circuit model was developed and experimentally validated. Large particle concentration factors were achieved by maintaining either average fluid velocity or Dean number throughout the entire length of the channel during the incremental removal of sample fluid. Also provided is the ability to simultaneously separate more than one particle from the same sample.

31 Claims, 12 Drawing Sheets

(51) Int. Cl.
*B01D 21/26* (2006.01)
*B01L 3/00* (2006.01)
*B01D 21/00* (2006.01)
*B01D 21/24* (2006.01)

(52) U.S. Cl.
CPC ...... *B01D 21/265* (2013.01); *B01L 3/502753* (2013.01); *B01L 3/502776* (2013.01); *G01N 1/4077* (2013.01); *B01L 2200/0636* (2013.01); *B01L 2200/0652* (2013.01); *B01L 2300/0816* (2013.01)

(58) Field of Classification Search
CPC ..... B01L 2200/0636; B01L 2200/0652; B01L 2300/0816
See application file for complete search history.

(56) References Cited

U.S. PATENT DOCUMENTS

| | | |
|---|---|---|
| 2009/0014360 A1 | 1/2009 | Toner et al. |
| 2009/0101575 A1 | 4/2009 | Alburty et al. |
| 2009/0283455 A1 | 11/2009 | Lean et al. |
| 2009/0283474 A1 | 11/2009 | Achard et al. |
| 2009/0283483 A1 | 11/2009 | Achard et al. |
| 2011/0096327 A1 | 4/2011 | Papautsky et al. |

PARTICLE SEPARATION AND CONCENTRATION USING SPIRAL INERTIAL FILTRATION

PRIORITY CLAIM

This application claims the benefit under 35 U.S.C. §119(e) of U.S. Provisional Application No. 61/707,878, filed Sep. 28, 2012, the disclosure of which is hereby incorporated by reference in its entirety.

FIELD OF THE INVENTION

The present invention relates to the field of microfluidics, and specifically relates to the field of sample preparation in microfluidics, including concentrating components of interest from samples. The present invention relates to methods of separating target components from biological samples such as blood sputum, etc. According to the present invention, the components of interests may be white blood cells, viruses, bacteria, fungi or combinations thereof. In some embodiments the components of interest may be cells having nuclei. In some embodiments the cells are mammalian cells. In some embodiments, the separated target organisms are subjected to treatment to release DNA which can then be recovered.

BACKGROUND OF THE INVENTION

High throughput particle separation and concentration are critical for many applications in the chemical, environmental, and biomedical fields. In particular, a number of cellular and sub-cellular purification and enrichment applications are used to enable the quantitative study and diagnosis of disease. The diagnosis of infectious diseases relies on the detection of relatively small amounts of infectious organisms (e.g., viruses, bacteria, or fungi) in the blood stream or in other biological samples. It may also be desirable to isolate other components from samples, including different types of cells (e.g., cancer cells, white blood cells, etc.). Once infectious organisms or components of interest are isolated from samples, they may then be used in further applications related to identification, including the isolation of nucleic acids from those components to allow downstream processing. Thus, a need exists for methods that provide for the enrichment and purification of components of interest from biological samples, including viruses, bacteria, fungi, cancer cells, and white blood cells.

Commercial products are available for cell separation, whole blood fractionation, and subcellular fractionation using density gradients. However, these techniques have poor separation resolution and are inappropriate for recovering rare cells. Commercially available fluorescence-activated cell sorting (FACS) systems enable automated cell separation and counting, but cannot process large sample volumes and are also inappropriate for recovering rare cells.

Many microfluidic techniques have emerged for sorting, concentrating, or purifying particles and cells.[1-20] Recent research into microfluidic devices has enabled applications that include microorganism recovery from environmental and biological samples[21], white blood cell counting for immune deficiency diagnosis[22], and circulating tumor cell (CTC) counting for cancer metastasis diagnosis and prognosis[23, 24]. Most of these techniques operate in the range of 1-100 µL/min, but a significantly higher throughput is needed for applications that require processing large volumes of fluid to obtain usable quantities of a target species, such as rare cell concentration. Methods designed for rare cell recovery must therefore be capable of significantly reducing the total fluid volume, from mL to 100 µL or less, to enable downstream microfluidic steps while preserving the rare targeted particles.

Recently, the need for high-throughput separation has been addressed by inertial-migration-based particle separation strategies, which are capable of achieving greater than 1 mL/min throughput.[25] These strategies balance forces within the channel to locate particles of a certain size into a desired longitudinal position. In a straight channel, two inertial lift forces ($F_L$), one due to the parabolic flow profile and the other due to the interaction of the particles with the wall, balance to focus particles to discrete equilibrium positions along the channel periphery.[26,27] This was first shown by Segre and Silberberg[28] at the centimeter-scale and later by others for microscale applications.[29-32, 21, 33-37]

The use of curvilinear geometries such as arc,[38-43] asymmetric serpentine,[44-46] and spiral[47-56] channels introduces a third force, the Dean force, $F_D$, due to the formation of secondary flows, known as Dean vortices. The magnitude of these secondary flows is described by the dimensionless Dean number (De)[57,58]

$$De = \frac{\rho U_f D_h}{\mu} \sqrt{\frac{D_h}{2R}} \quad (1)$$

where ρ is the density of the fluid, $U_f$ is the average fluid velocity, µ is the fluid dynamic viscosity, R is the radius of curvature of the curvilinear channel, and $D_h$, is the hydraulic diameter. The hydraulic diameter, $D_h$, is determined from $$D_h = \frac{2wh}{w+h} \quad (2)$$

where w and h are the channel width and height, respectively. The Dean vortices are counter-rotating and act to laterally displace particles across the channel by imposing a drag force. The Dean force acts in combination with the combined lift forces to alter the equilibrium positions of focused particles to a single equilibrium position near the inner wall of the channel.

FIG. 1A is a schematic diagram of a microfluidic channel cross-section illustrating the principle of inertial spiral microfluidics. The main flow (into the page) follows a curvilinear path leading to the development of secondary flows, known as Dean vortices (dashed lines). Dispersed particles experience a combination of lift forces ($F_L$) and Dean forces ($F_D$), which result in differential migration of the particles to unique equilibrium positions near the inner wall.

The lift forces go as $F_L \propto a_p^4$ and the Dean forces go as $F_D \propto a_p$, where $a_p$ is particle diameter. The equilibrium position is thus particle-size-dependent, with larger particles (dominated by $F_L$) aligning near the inner wall and smaller particles (dominated by $F_D$) near the channel center[47]. An example of a two-particle separation in a microfluidic spiral is shown in FIG. 1B. Particles of one size (e.g., 15 µm) are separated from particles of a different size (e.g., 8 µm) at a flow rate of 1 mL/min.

Spiral inertial microfluidic devices have been successfully used in a wide range of applications including particle[47,49,51,54] and cell[49] separations, cell synchronization,[50] circulating tumor cell isolation,[59] and electroporation.[55] These devices typically utilize a branched outlet to collect the concentrated, focused particle or cell streams. The separation efficiency for a device is defined as the number of targeted particles collected at a single outlet over the number of those particles input into the device. The concentration factor is defined as the concentration of particles, assuming 100% recovery, over the inlet partial concentration multiplied by the separation efficiency. Ultimately, for any geometry, the concentration factor is limited by the number of outlets: if there are too many, a particle stream cannot be precisely controlled to flow through a single one. Devices with branched outlets of up to eight channels have been shown[49]. This resulted in a concentration factor of 8× (i.e., 87.5% removal of the inlet fluid). Using only branched outlets, however, further increases in concentration factor to greater than 10× (90% fluid removal) are challenging. For example, 93% removal corresponds to a 14× concentration factor, which would require 14 outlets. The width of the outlets typically needs to be 4-5 times the particle diameter to ensure that the particle stream is collected in a single outlet. A large number of outlets, therefore, thus requires a large expansion of the width of the channel in front of the outlets. This expansion is accompanied by a corresponding increase in the width of the fluid streamlines, and thus the width of the particle stream, which becomes too wide to be collected in a single outlet channel, leading to particle loss and a decrease in separation efficiency.

Increasing particle concentration and purity in a microfluidic device by removing, or "skimming", fluid from a main channel through microfluidic waste channels has been previously reported. Traditional skimming techniques rely on the natural formation of small particle-free regions near channel walls[60-64] (as shown in FIG. 2A) or geometrical features[65] (as shown at FIG. 2B). In one approach, posts[66,67] or dams[68] located at the outer wall were used to filter particles. Fluid and smaller particles were able to pass through the post or dam filters and were removed, while larger particles were retained. These devices were operated at low flow rates (<100 μL/min) in order to minimize the inertial effects and the secondary Dean flows. As a result, centrifugal forces dominated and pushed particles to the outside wall of the curvilinear channels. Another design took advantage of centrifugal forces to push blood cells against the outer wall and remove plasma from a waste channel on the inner wall.[38] Flow rates up to 120 μL/min were achieved. In a third approach, inertial lift forces focused targeted cells away from the walls, creating a target-free region where waste channels removed fluid and non-targeted cells[69,70]; this design achieved >500 μL/min. These devices focused on enriching targeted cells relative to high-concentration, non-targeted species, and were not aiming to achieve high concentration factors.

SUMMARY OF THE INVENTION

The present invention relates to methods of separating particles within samples, for example, separating target DNA, from mixed DNA in a sample. In some, non-limiting embodiments, the target DNA is present in target organisms, such as viruses, bacteria (prokaryotes), fungi or combinations thereof. In some embodiments the mixed DNA includes target DNA and non-target DNA. In some embodiments, the non-target DNA is mammalian DNA. In some embodiments the sample contains cells having nuclei. In some embodiments the cells are mammalian cells. In some embodiments, the separated target organisms are treated to release their DNA which can be recovered.

In one embodiment of the present invention, there is provided a method of designing a spiral inertial filtration device as provided herein.

In a second embodiment of the present invention, there is provided a method of separating a component of interest from a sample comprising introducing the sample to a spiral inertial filtration device as provided herein.

In a further embodiment, the spiral inertial filtration device comprises at least one waste channel configured to draw particle-free fluid from the device, thereby increasing the particle concentration of fluid (sample) remaining in the device.

In another embodiment, the waste channels reduce the volume of the sample from about 10% to about 95%, ie. about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%.

In a further embodiment, the component of interest is concentrated by the spiral inertial filtration device.

In another embodiment, the component of interest is selected from viruses, bacteria, fungi, cancer cells, and white blood cells. In a further embodiment, the component of interest is neutrophils.

One embodiment of the present invention provides a spiral inertial filtration device as described herein.

Another embodiment of the present invention provides a spiral inertial filtration device as described herein, wherein the device concentrates and/or filters more than one component of interest from the same sample.

A further embodiment of the present invention provides a method of concentrating and/or filtering more than one component of interest from a sample using a spiral inertial filtration device as provided herein.

In particular, aspects of the invention are embodied in a fluid processing apparatus configured for separating particles from a fluid flowing through the apparatus and comprising a fluid inlet, a main fluid channel, one or more outlets, and one or more secondary channels. The fluid inlet configured to receive a fluid containing particles having one or more particle sizes. The a main fluid channel extends from the fluid inlet, is arranged in a spiral configuration, and is configured to cause differential migration of particles within the fluid flowing through the main fluid channel into unique equilibrium positions within the main channel according to the size of the particle, thereby forming one or more particle streams and a particle-free region within the fluid flowing through the main channel. The one or more outlets are in fluid communication with the main fluid channel and are configured to receive particles from a particle stream flowing from the main fluid channel. The one or more secondary channels extend from the main fluid channel and are configured to draw at least a portion of the fluid from the particle-free region within the main channel to increase the concentration of particles within the remaining fluid flowing through the main channel.

According to further aspects of the invention, the particles of each of the one or more particle streams is maintained in an equilibrium position by lift forces $F_L$ and Dean forces $F_D$.

According to further aspects of the invention, the one or more particles sizes are in a range of 4.8 μm to 15 μm.

According to further aspects of the invention, the secondary channels are configured to draw a portion of the fluid of the particle-free region from the main channel to reduce the volume of fluid flowing through the main channel by about 10-95%.

According to further aspects of the invention, the particles are selected from the group consisting of DNA molecules, viruses, bacteria, fungi, cancer cells, white blood cells, and neutrophils.

According to further aspects of the invention, the fluid flowing through the apparatus comprises a sample and the particles comprise more than one component of interest within the sample, and the fluid inlet is configured to receive the sample, the main fluid channel is configured so that the components of interest are focused into more than one component stream according to the size of the components, thereby forming a component-free region within the fluid flowing through the main channel, the apparatus includes more than one outlet in fluid communication with the main fluid channel and configured to receive the components of interest from the component streams flowing from the main fluid channel to filter each of the components of interest from the sample, and the one or more secondary channels are configured to draw at least a portion of the fluid from the component-free region within the main channel to increase the concentration of components of interest within the remaining fluid flowing through the main channel.

According to further aspects of the invention, the fluid inlet is located at an inner end portion of the spiral configuration of the main channel, the one or more outlets are located at an outer end portion of the spiral configuration of the main channel, and the one or more secondary channels extend radially outwardly from an outer loop of the spiral configuration of the main channel.

According to further aspects of the invention, the main channel has a non-uniform width varying along the length of the main channel.

According to further aspects of the invention, the apparatus includes at least two secondary channels, and the width of the main channel is substantially constant between each two neighboring secondary channels.

According to further aspects of the invention, the geometry of the main channel is changed following a secondary channel to compensate for fluid removal via the secondary channel.

According to further aspects of the invention, the geometry of the main channel is changed following a secondary channel to maintain a constant or substantially constant flow velocity within the main channel before and after the secondary channel.

According to further aspects of the invention, the geometry of the main channel is changed by changing the width of the main channel, and the new width $w_{m,j}$ of the main channel following a $j^{th}$ secondary channel is determined by the formula:

$$w_{m,j-1} = x_{m,j-1} w_{m,j},$$

wherein $x_{m,j-1}$ is the fraction of fluid remaining in the main channel after fluid removal through the $j^{th}$ secondary channel, and $w_{m,j}$ is the width of the previous section of the main channel.

According to further aspects of the invention, the geometry of the main channel is changed following a secondary channel to maintain a constant or substantially constant Dean number, $D_e$, within the main channel before and after the secondary channel, wherein the Dean number, $D_e$, is given by the formula:

$$De = \frac{\rho U_f D_h}{\mu} \sqrt{\frac{D_h}{2R}}$$

wherein $\rho$ is the density of the fluid, $U_f$ is average fluid velocity, $\mu$ is fluid dynamic viscosity, R is the radius of curvature of the main channel, and $D_h$ is a hydraulic diameter, and wherein the hydraulic diameter, $D_h$, is determined from:

$$D_h = \frac{2wh}{w+h},$$

wherein w is the width of the main channel and h is the height of the main channel.

According to further aspects of the invention, the geometry of the main channel is changed by changing the width of the main channel.

According to further aspects of the invention, a downstream corner of a junction between the main channel and the secondary channel is filleted to allow for a gradual change in the width of the main channel.

According to further aspects of the invention, that apparatus comprises between one and five outlets.

According to further aspects of the invention, that apparatus comprises between one and six secondary channels.

According to further aspects of the invention, each secondary channel extends from an outer edge of an outer-most ring of the spiral configuration of the main channel.

According to further aspects of the invention, each of the one or more secondary channels is configured to draw from 5 to 50% of the fluid flowing through the main channel.

According to further aspects of the invention, each secondary channel comprises a meander path.

According to further aspects of the invention, the apparatus is fabricated from polydimethylsiloxane.

According to further aspects of the invention, the apparatus is configured to accommodate a flow rate of between 100 μL/min and 1250 μL/min.

According to further aspects of the invention, the apparatus is configured to process fluid at a rate of 1 mL/min.

According to further aspects of the invention, the width of each secondary channel is set to draw a specified portion of the fluid of the particle-free region from the main channel according to the formula:

$$w \approx \frac{12\mu L}{h^3 R_H} + 0.63h,$$

wherein w is the width of the secondary channel, h is the height of the secondary channel, L is the length of the secondary channel, μ is the dynamic viscosity of the fluid, and $R_H$ is the hydraulic resistance of the secondary channel.

According to further aspects of the invention the fluid resistance of a secondary channel required to draw fluid from the main channel at a specified rate satisfies the relationship:

$$R_{s,j} = r_{Q,j}\left(R_{m,j} + \frac{R_{s,j-1}}{1+r_{Q,j-1}}\right)$$

where $R_{s,j}$ is the fluid resistance of the $j^{th}$ secondary channel at the $j^{th}$ node where the $j^{th}$ secondary channel connects to the main channel, $R_{m,j}$ is the fluid resistance of the main channel at the $j^{th}$ node, $R_{s,j-1}$ is the fluid resistance of the secondary channel at a previous node j−1, and $r_{Q,j-1}$ is the volumetric flow ratio of flow within the main channel ($Q_{m,j}$) to flow within the secondary channel ($Q_{s,j}$) at the $j^{th}$ node.

According to further aspects of the invention, the spiral configuration of the main channel comprises a 6 or 7-loop spiral.

According to further aspects of the invention, the main channel comprises a width of about 250 μm and a height of about 50 μm.

According to further aspects of the invention, the apparatus comprises a single inlet, a single secondary channel, and a bifurcating outlet, and the spiral main channel has a 250 μm gap between successive loops.

According to further aspects of the invention, the spiral configuration is an Archimedean spiral.

According to further aspects of the invention, the width of the secondary channel is between 40 and 250 μm According to further aspects of the invention, the length of the secondary channel is about 19 mm.

According to further aspects of the invention, each secondary channel comprises a width of about 35 μm, a height of about 50 μm, and a length of about 19 mm.

Further aspects of the invention are embodied in a method of filtering and/or concentrating particles of a fluid containing particles of one or more particle sizes. A fluid is moved in a spiral path under conditions that cause differential migration of particles within the moving fluid into unique equilibrium positions according to the size of the particle thereby forming one or more particle streams and a particle-free region within the moving fluid. At least a portion of the fluid is drawn from the particle-free region of the moving fluid to increase the concentration of particles within the remainder of the moving fluid, and particles from one or more of the particle streams are collected.

According to further aspects of the invention, the collecting step is performed at the end of the spiral path.

According to further aspects of the invention, the particles comprise one or more components of interest within a sample fluid.

According to further aspects of the invention, the method further comprises increasing the concentration of each component of interest.

According to further aspects of the invention, the particles of each of the one or more particle streams are maintained in equilibrium positions by lift forces $F_L$ and Dean forces $F_D$.

According to further aspects of the invention, the one or more particles sizes are in a range of 4.8 μm to 15 μm.

According to further aspects of the invention, the drawing step reduces the volume of the moving fluid by about 10-95%.

According to further aspects of the invention, the particles are selected from the group consisting of DNA molecules, viruses, bacteria, fungi, cancer cells, white blood cells, and neutrophils.

According to further aspects of the invention, the method further comprises changing the conditions of the moving fluid after drawing at least a portion of the fluid from the particle-free region of the moving fluid to compensate for fluid removal.

According to further aspects of the invention, the method further comprises changing the conditions of the moving fluid after drawing at least a portion of the fluid from the particle-free region of the moving fluid to maintain a constant or substantially constant flow velocity within the moving fluid before and after drawing at least a portion of the fluid from the particle-free region of the moving fluid.

According to further aspects of the invention, the method further comprises changing the conditions of the moving fluid after drawing at least a portion of the fluid from the particle-free region of the moving fluid to maintain a constant or substantially constant Dean number before and after drawing at least a portion of the fluid from the particle-free region of the moving fluid.

41. The method of claim 30, wherein the moving fluid comprises a flow rate of between 100 μL/min and 1250 μL/min.

According to further aspects of the invention, the method comprises filtering and/or concentrating fluid containing particles of one or more particle sizes at a rate of 1 mL/min.

According to further aspects of the invention, the step of moving fluid in a spiral path is performed in a main fluid channel extending from a fluid inlet and arranged in a spiral configuration, the step of drawing at least a portion of the fluid from the particle-free region of the moving fluid is performed in one or more secondary channels extending from the main fluid channel, and the step of collecting particles from one or more of the particle streams is performed with one or more outlets in fluid communication with the main fluid channel.

According to further aspects of the invention, the main channel has a non-uniform width varying along the length of the main channel.

According to further aspects of the invention, the step of drawing at least a portion of the fluid from the particle-free region of the moving fluid is performed by at least two secondary channels, and the width of the main channel is substantially constant between each two neighboring secondary channels.

According to further aspects of the invention, the one or more secondary channels extend radially outwardly from an outer loop of the spiral configuration of the main channel.

According to further aspects of the invention, the method further comprises changing the geometry of the main channel following a secondary channel to compensate for fluid removal via the secondary channel.

According to further aspects of the invention, the method further comprisies changing the geometry of the main channel following the secondary channel to maintain a constant or substantially constant flow velocity within the main channel before and after the secondary channel.

According to further aspects of the invention, the method further comprises changing the geometry of the main channel by changing the width of the main channel, and the new width $w_{m,j}$ of the main channel following a $j^{th}$ secondary channel is determined by the formula:

$$w_{m,j-1} = x_{m,j-1} w_{m,j},$$

wherein $x_{m,j-1}$ is the fraction of fluid remaining in the main channel after fluid removal through the $j^{th}$ secondary channel, and $w_{m,j}$ is the width of the previous section of the main channel.

According to further aspects of the invention, the method further comprises changing the geometry of the main channel following a secondary channel to maintain a constant or substantially constant Dean number, $D_e$, within the main channel before and after the secondary channel, the Dean number, $D_e$, is given by the formula:

$$De = \frac{\rho U_f D_h}{\mu} \sqrt{\frac{D_h}{2R}}$$

and $\rho$ is the density of the fluid, $U_f$ is average fluid velocity, $\mu$ is fluid dynamic viscosity, R is the radius of curvature of the main channel, and $D_h$ is a hydraulic diameter, and the hydraulic diameter, $D_h$, is determined from:

$$D_h = \frac{2wh}{w+h},$$

and w is the width of the main channel and h is the height of the main channel.

According to further aspects of the invention, the fluid resistance of a secondary channel required to draw fluid from the main channel at a specified rate satisfies the relationship:

$$R_{s,j} = r_{Q,j}\left(R_{m,j} + \frac{R_{s,j-1}}{1 + r_{Q,j-1}}\right)$$

where $R_{s,j}$ is the fluid resistance of the $j^{th}$ secondary channel at the $j^{th}$ node where the $j^{th}$ secondary channel connects to said main channel, $R_{m,j}$, is the fluid resistance of said main channel at the $j^{th}$ node, $R_{s,j-1}$ is the fluid resistance of the secondary channel at a previous node j−1, and $r_{Q,j-1}$ is the volumetric flow ratio of flow within said main channel ($Q_{m,j}$) to flow within the secondary channel ($Q_{s,j}$) at the $j^{th}$ node.

According to further aspects of the invention, the method further comprises changing the geometry of the main channel by changing the width of the main channel.

According to further aspects of the invention, the method further comprises collecting particles from each particle stream with between one and five outlets.

According to further aspects of the invention, the method further comprises drawing at least a portion of the fluid from the particle-free region of the moving fluid with between one and six secondary channels.

According to further aspects of the invention, each secondary channel extends from an outer edge of an outer-most ring of the spiral configuration of the main channel.

According to further aspects of the invention, the method comprises drawing from 5 to 50% of the moving fluid in the main channel with each of the one or more secondary channels.

According to further aspects of the invention, the method further comprises defining the width of each secondary channel to draw a specified portion of the fluid of the particle-free region from the main channel according to the formula:

$$w \approx \frac{12\mu L}{h^3 R_H} + 0.63h,$$

wherein w is the width of the secondary channel, h is the height of the secondary channel, L is the length of the secondary channel, $\mu$ is the dynamic viscosity of the fluid, and $R_H$ is the hydraulic resistance of the secondary channel.

According to further aspects of the invention, the spiral configuration of the main channel comprises a 7-loop spiral having an inner radius of about 0.5 cm, and the main channel comprises a width of about 250 µm and a height of about 50 µm.

According to further aspects of the invention, the spiral main channel has a 250 µm gap between successive loops.

According to further aspects of the invention, the width of each secondary channel is between 40 and 250 µm According to further aspects of the invention, the length of each secondary channel is about 19 mm.

According to further aspects of the invention, each secondary channel comprises a width of about 35 µm, a height of about 50 µm, and a length of about 19 mm.

Further aspects of the invention are embodied in a method of separating one or more components of interest from a sample fluid, comprising the steps of moving the sample fluid in a spiral path under conditions that cause the component(s) of interest within the moving sample fluid to be focused into one or more component streams according to component size, thereby forming a component-free region within the moving sample fluid, drawing at least a portion of the sample fluid from the component-free region of the moving sample fluid to increase the concentration of component(s) of interest within the remainder of the moving sample fluid, and collecting the component(s) of interest from one or more of the component streams.

The above and other embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers or labels indicate identical or functionally similar elements.

DETAILED DESCRIPTION OF THE EXEMPLARY EMBODIMENTS

Figure 1A:
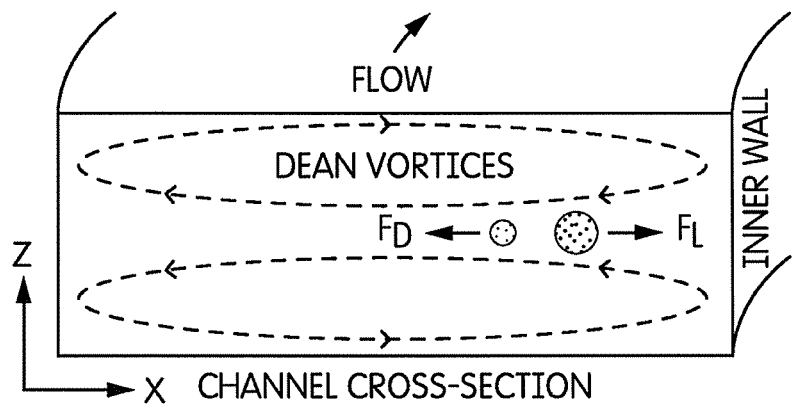
FIG. 1A is a schematic diagram of a microfluidic channel cross-section, illustrating the principle of inertial spiral microfluidics according to prior art.

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

Unless defined otherwise, all terms of art, notations and other technical terms or terminology used herein have the same meaning as is commonly understood by one of ordinary skill in the art to which this disclosure belongs. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, in front of, behind, next to, adjacent, between, horizontal, vertical, diagonal, longitudinal, transverse, etc., are used for convenience in referring to such component, apparatus, location, feature, or a portion thereof in the drawings and are not intended to be limiting.

Furthermore, unless otherwise stated, and specific dimensions mentioned in this description are merely representative of an exemplary implantation of a device embodying aspects of the invention and are not intended to be limiting.

The present invention relates to methods of separating particles, such as target DNA, from mixed DNA in a sample. In some embodiments, the target DNA is present in target organisms. In some embodiments, the target organisms may be viruses, bacteria (prokaryotes), fungi or combinations thereof. In some embodiments the mixed DNA includes target DNA and non-target DNA. In some embodiments, the non-target DNA is mammalian DNA. In some embodiments the sample contains cells having nuclei. In some embodiments the cells are mammalian cells. In some embodiments, the separated target organisms are treated to release their DNA which can be recovered.

Figure 3:
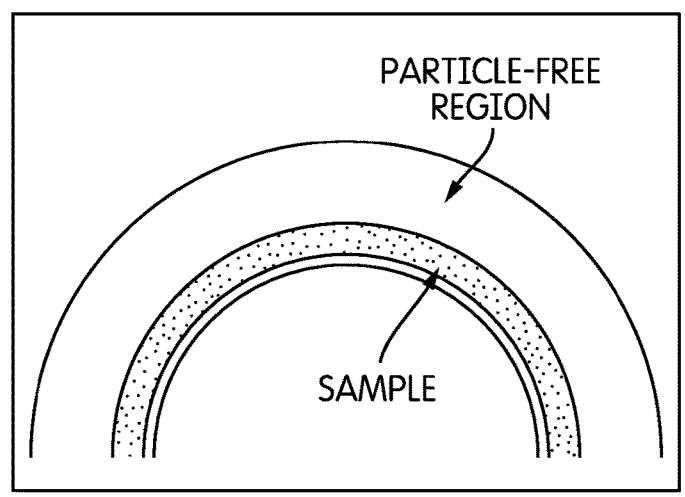
FIG. 3 is a schematic diagram illustrating the creation of particle-free flow region in a curvilinear channel.

Thus, the present invention provides a method of increasing the concentration factor of spiral inertial microfluidics while relaxing the requirements for the number of branched outlets, through a new approach known as Spiral Inertial FilTration (SIFT). This technique utilizes the focusing behavior of inertial microfluidics in a main microfluidic channel having a spiral geometry to create a large particle-free flow region from which a large fraction of particle-free (or substantially particle free) fluid can be "skimmed" through one or more waste channels, or secondary channels, extending from one or more portions of the main channel. The major drawback of skimming techniques described above is that the performance drops at increased flow rates. In SIFT, particles are instead focused near the inner wall, creating a large particle-free region at the outer wall (as shown in FIG. 3). In accordance with aspects of the invention, by utilizing side waste channels that extend away from the outer wall of the main, spiral channel, fluid can be removed from this particle-free region, thus increasing the concentration of the particles in the main microfluidic channel. In addition, due to the focusing nature of spiral inertial microfluidics, the particle streams are minimally disrupted by removing large amounts of fluid.

Figure 4:
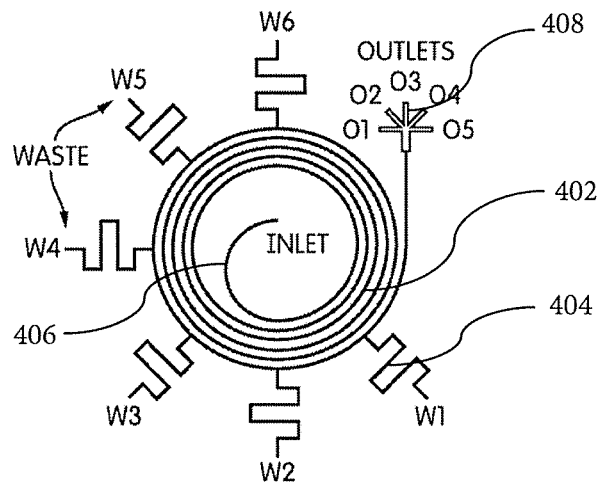
FIG. 4 is a schematic diagram of a spiral inertial filtration (SIFT) device embodying aspects of the invention.

Leveraging this concept, the SIFT system utilizes waste channels extending from the outer edge of the outer-most ring of the spiral to generate a large concentration factor. FIG. 4 is a schematic diagram of a spiral inertial filtration (SIFT) device embodying aspects of the invention. The device includes an inlet (406) at which a fluid containing particles of one or more sizes is introduced into the device (400), a microfluidic, main channel (402) coiled in a spiral configuration, and one or more outlets (408). In the illustrated embodiment, the device includes five outlets O1-O5. In practice, however, the device (400) may have fewer than or more than five outlets (408). In the illustrated embodiment, the inlet (406) is located at an inner part of the spiral configuration of the main channel (402), and the outlets O1-O5 are located at an outer end portion of the spiral configuration. As the fluid flows through the main channel from the inlet (406) toward the outlets, the particles within the fluid segregate into separate, focused streams, according to the size of the particle, as explained above, thereby creating substantially particle-free regions within the fluid flowing through the main channel. Fluid (particle-free or substantially particle-free) is removed from the main spiral channel through one or more waste, or secondary, channels (404) labeled W1-W6 starting closest to the outlet(s). The illustrated embodiment include six secondary channels W1-W6. In practice, the device may have fewer than or more than six secondary channels (404). In the illustrated embodiment, the waste channels (404) extend radially outwardly from the outermost loop of the spiral configuration. Concentrated particle streams, each comprising particles of a different size, are collected through one of outlets O1-O5. The device (400) may be fabricated from a material such as polydimethylsiloxane (PDMS) prepolymer, examples of which are described in further detail below. Other suitable materials include thermal plastics (e.g., Poly(methyl methacrylate) ("PMMA"), or Cyclic Olefin Copolymer ("COC")) and glass/silicon.

Figure 1B:
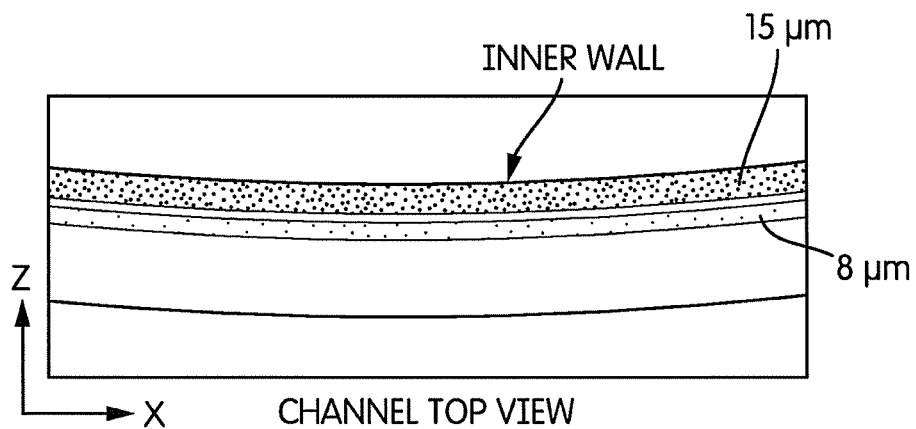
FIG. 1B is a top view of a portion of a spiral microfluidic channel according to prior art illustrating differential migration of particles into unique equilibrium positions according to the size of the particle thereby forming discrete, focused particle streams and a particle-free region within the channel.
Figure 2A:
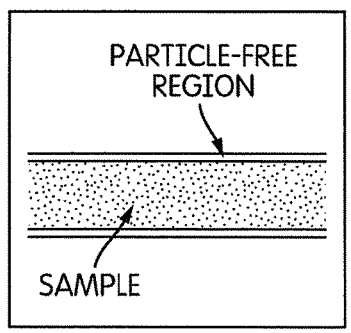
FIGS. 2A and 2B are prior art schematic diagrams illustrating the creation of particle-free flow regions in straight channels (FIG. 2A) and expansions (FIG. 2B).
Figure 2B:
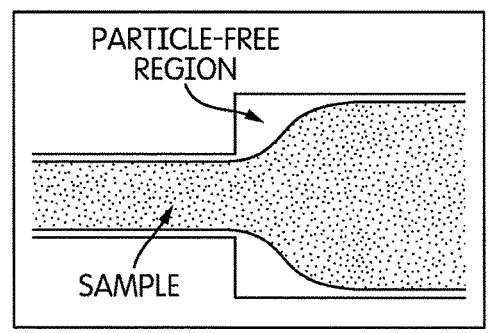

In other implementations, the particle, or component, of interest does not readily migrate to a unique equilibrium position under the effects of lift forces ($F_L$) and/or Dean forces ($F_D$), and thus does not focus into a discrete particle stream as shown in FIG. 1B. For example, viruses and bacteria can, in some circumstance, be difficult to separate from a flow stream using the inertial filtration techniques described herein. Such non-focused components can be collected through the secondary channels and can be focused by other means and removed from the waste fluid.

It was demonstrated that the SIFT design concept presented in FIG. 4 is capable of recovering a targeted particle size with nearly perfect separation efficiency and concentrating the targeted particles by more than an order of magnitude while operating at a sample processing rate of 1 mL/min. Aspects of the invention include the development of equations for designing a SIFT device for specific fluid removal. Validation of the design equations was demonstrated by removal of a desired fraction of the sample fluid (without removing targeted particles) by controlling the channel geometries. The experimental results demonstrated that the amount of fluid removed from the sample is limited by changes in particle position and particle stream width caused by decreases in the linear velocity in the channel, $U_f$, and the Dean number, De, as fluid is removed.

Aspects of the invention further include the determination that the limitations on larger fluid removal rates can be overcome by correcting the main channel geometry to maintain $U_f$ or De following fluid removal through a waste channel. Finally, separation and recovery of two particle sizes (4.8 μm and 8 μm) was demonstrated using a SIFT device with 6 waste channels (404) and 5 outlets (408) (as in the device of FIG. 4). The particle sizes selected were for demonstration purposes and are not limiting as to the scope of the invention as the invention may be implemented to filter and/or concentrate particles of other sizes as we. Using this design, nearly 100% separation efficiency of the two particle sizes was demonstrated while removing 93% of the inlet fluid, which leads to a 13× concentration increase of each of the recovered particle sizes.

Spiral Inertial Filtration Design Principle

Figure 5A:
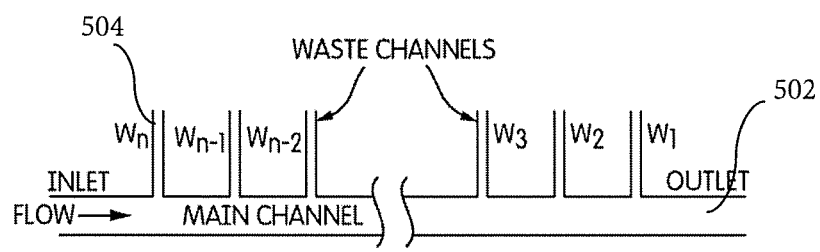
FIG. 5A is a schematic diagram of a fluidic network including a main channel and a plurality of waste, or secondary, channels extending from the main channel.
Figure 5B:
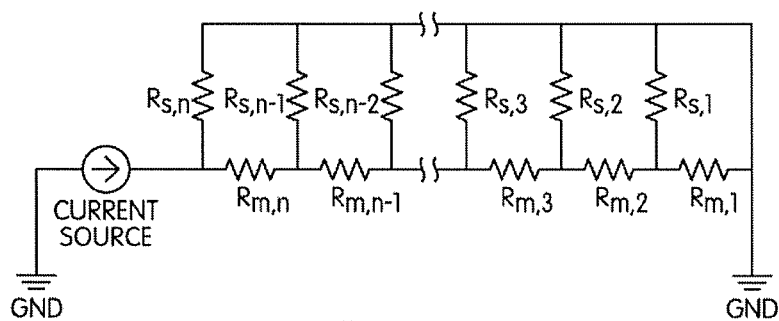
FIG. 5B is a diagram of an equivalent circuit analog used to design an apparatus embodying aspects of the present invention.

For the derivation of equations for designing waste channels configured for the removal of specific volumes of fluid from the SIFT devices, an equivalent circuit analog[60,71] was used. The volumetric flow rate (Q) was determined using $$\Delta P = Q R_H \quad (3)$$

where $\Delta P$ is the pressure drop and $R_H$ is the fluidic resistance. The flow removed by any given waste channel is specified by the ratio of fluidic resistances of the waste channel and the main channel. FIG. 5A is a schematic diagram of a fluidic network including a main channel (502) and a plurality of waste, or secondary, $W_1$-$W_n$ channels (504). A schematic of the equivalent electrical circuit is shown in FIG. 5B. The subscripts "m" and "s" represent the main channel and secondary channels, respectively. The flow rate at the inlet of the device is analogous to a current source, and all outlets are terminated at ground, as they have the same pressure. For a volumetric flow ratio, $r_{Q,j}$, of the main channel ($Q_{m,j}$) to a side waste channel at the $j^{th}$ node ($Q_{s,j}$), the resistance relationship between the main and waste channels satisfies $$R_{s,j} = r_{Q,j}\left(R_{m,j} + \frac{R_{s,j-1}}{1 + r_{Q,j-1}}\right) \quad (4)$$

where $R_{s,j}$ and $R_{m,j}$ are the resistances of the waste channel and main channel at the $j^{th}$ node, respectively, $R_{s,j-1}$ is the resistance of the waste channel at the previous node j−1, and $r_{Q,j-1}$ is the volumetric flow ratio at the previous node (see below for a derivation of Equation (4))—this holds for j=2, 3, 4, . . . , n−1, n. For j=1, the resistance is simply $R_{s,1} = r_{Q,1} R_{m,1}$. The entire circuit does not need to be solved simultaneously. Equation (4) illustrates that once $r_{Q,j}$ is specified, the resistance of the waste channel, $R_{s,j}$, at any node is determined only by the resistance in the main channel, $R_{m,j}$ the resistance of the previous waste channel, $R_{s,j-1}$, and the flow ratio of the previous waste channel, $r_{Q,j-1}$. Using this relationship, the resistance required to achieve a specified fluid removal can be determined, and from that relationship, the geometry, e.g., the width, of the secondary waste channel can be determined.

Once the resistances of the main channel and the waste channels are calculated, the channel dimensions can be calculated. For w>h or w≈h, the hydraulic resistance of a square duct is given by[72]

$$R_H = \frac{12\mu L}{wh^3}\left(1 - \frac{192h}{\pi^5 w}\sum_{n=1,3,5,\ldots}^{\infty} \frac{\tanh\left(\frac{n\pi w}{2h}\right)}{n^5}\right)^{-1} \quad (5)$$

where μ is the fluid dynamic viscosity and w, h, and L are the width, height, and length of the channel. If w>h, Equation (5) simplifies to[72]

$$R_H \approx \frac{12\mu L}{wh^3\left(1 - 0.63\frac{h}{w}\right)}. \quad (6)$$

Assuming constant L and h, Equation (6) illustrates that the fluidic resistance of a waste channel can be controlled by changing its width. Thus, amount of fluid drawn through a secondary channel can be controlled by the width of the secondary channel, which is given by the formula:

$$w \approx \frac{12\mu L}{h^3 R_H} + 0.63h, \quad (7)$$

The lengths for curvilinear channel sections of the spiral, $L_{arc}$, were calculated using $$L_{arc} = \frac{\alpha \pi R}{180},$$

where $\alpha$ is the angle in degrees and R is the radius of curvature.

Equation (7) is only valid for the case of w>h. However, when attempting to remove only a small fraction of fluid, a thin channel may be required, and thus the width may be less than the height. For this case, the full Equation (5) should be solved to determine the width, which requires a numerical solver.

To design the system for a targeted performance, the waste channel width is set in order to remove a targeted fraction of the sample fluid. The fraction of fluid removed through a waste channel, $x_{s,j}$, is related to $r_{Q,j}$ through $$x_{s,j} = \frac{1}{1 + r_{Q,j}} \quad (8)$$

where the fraction of the flow remaining in the main channel, $x_{m,j}$, is given by $$x_{m,j} = \frac{r_{Q,j}}{1 + r_{Q,j}}. \quad (9)$$

By simply specifying the ratio of volumetric flow between the main channel and a waste channel ($r_{Q,j}$), a spiral inertial filtration device can be designed for the removal of a specific fraction of the inlet fluid.

Validation of Design Equations

Figure 6A:
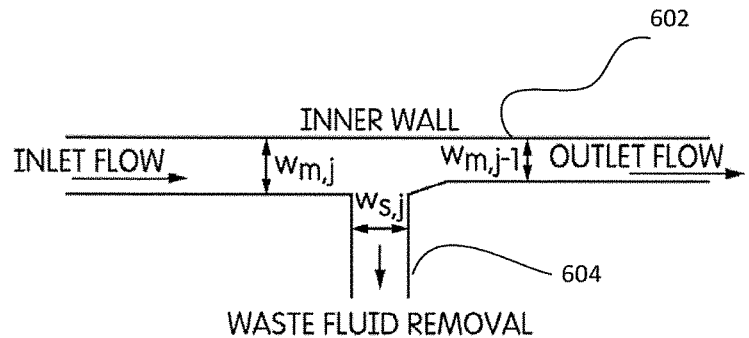
FIG. 6A is a schematic diagram illustrating the dimensions of a device with a main channel and a single waste channel located at the W2 position of the device shown in FIG. 4.

The rate of fluid removal from the main channel via the secondary, or waste, channel is controlled by designing for a specific flow ratio ($r_Q=Q_m/Q_s$) of main channel flow to secondary channel flow. The relative volumetric flow rates through the main ($Q_m$) and secondary channel ($Q_s$) are achieved by properly balancing the fluidic resistances in the channels. Thus, the fraction of fluid removed from a SIFT device can be controlled by designing for a specific flow ratio, $r_{Q,j}$, at each waste channel, which is achieved by properly balancing the fluidic resistances. To verify the design defined by the equations derived above, devices designed for removal of 5, 10, 20, and 50% of the inlet fluid through a single waste channel were fabricated and tested. The waste channel was located at the W2 position (See FIG. 4). A schematic of the waste channel is shown in FIG. 6A. As described above, the width of the waste channel, $w_{s,j}$, was set to control the amount of fluid removed from the main channel. The main channel width prior to the waste channel, $w_{m,j}$, and the main channel width after the waste channel, $w_{m,j-1}$, were both 250 µm.

Figure 6B:
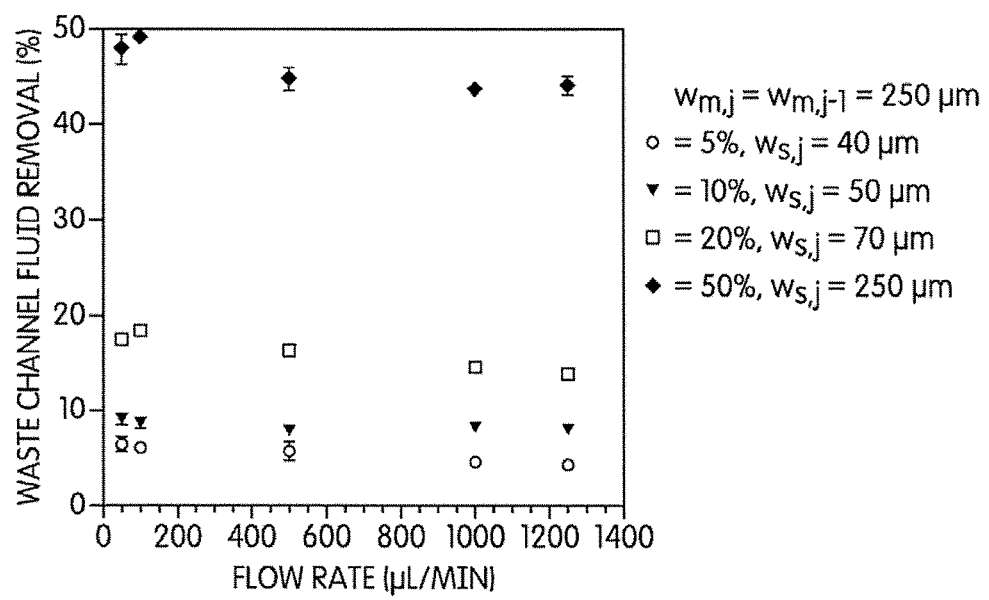
FIG. 6B is a graph showing dependency of actual fluid removed from a waste channel—as a percentage of fluid introduced at the inlet and flowing in the main channel—on the fluid flow rate for waste channels designed for 5%, 10%, 20%, and 50% fluid removal.

FIG. 6B shows the percentage of fluid removed through the waste channel (604) as a function of inlet volumetric flow rate for devices designed for the removal of 5%, 10%, 20%, or 50% of the inlet fluid. The widths of the main channel (602) $w_m$ and the waste, or secondary, channels (604) $w_s$ in µm are listed for each of the devices. The width of the main channel (602), $w_{m,j}$, before the waste channel (604) is equal to the width of the main channel (604) after the waste channel (604), $w_{m,j-1}$ for each graph presented in FIG. 6B. The width of the waste channel (604), $w_{s,j}$, however, is shown as being different for each graph in response to the amount of fluid removed from the main channel (602). Specifically, the width of the main channel (602), $w_{m,j}$, before the waste channel (604) and after the waste channel, $w_{m,j-1}$, is 250 µm. Errors bars indicate the standard deviation across three experiments for a single device. To measure variation due to fabrication, two conditions were tested with duplicate devices: 20% fluid removal at 50 µL/min and 10% fluid removal at 1000 µL/min. The 20% results agreed to within 1.5%, and the 10% results were within 0.5%.

At low flow rates, the fraction of fluid removed was within 2% of the designed value. With increasing flow rate, the fraction decreased, flattening at 1000 µL/min, although the removal rates were still within 6%. According to Equation (4), the fluid removal rate should be independent of flow rate. The flow rate dependence was attributed to the elasticity of the PDMS. It is known that deformation of PDMS microchannels occurs under pressure-driven flow, causing changes in the channel height and width[73,74]. The design equations did not account for this behavior. As a result, for the flow rates at which operation was desired (>750 µL/min), the fluid removal rates were different than what was designed. The widths of the waste channels could be adjusted to account for PDMS deformation, or other materials can be used that do not swell under pressure, such as thermal plastics.

Equation (7) was used to design these devices even though for the 5% removal width, w, of the waste channel is less than height, h, of the waste channel so this approximation was not valid. For that 5% device, the difference in widths calculated by solving Equation (5) and Equation (7) is 5 µm. Given the fabrication tolerances (see above), a 5 µm difference in the widths was deemed to be acceptable. FIG. 6B shows 5% fluid removal to within ±1.5%.

EXAMPLES

Example 1: Device Fabrication

To evaluate the design methodology, a series of SIFT microfluidic devices with a single waste channel (at the W2 position in FIG. 4) were fabricated. These devices consisted of a 7-loop Archimedean spiral (inner radius of 0.5 cm) with a single inlet, a waste channel, and a bifurcating outlet. In this non-limiting example, the spiral channel was 250 µm×50 µm (w×h) and had a 250 µm gap between successive loops. The evaluation design chosen is not intended to be limiting. The invention may be implemented with main channel conigurations having fewer than or more than seven loops or configurations other than an Archimedean spiral of the stated dimensions. The widths of the waste channels were set between 40 and 250 µm to remove a certain fraction of fluid: e.g., 5, 10, 20, or 50%. As discussed below, the flow removed by a waste channel depends on its fluidic resistance, which is proportional to the channel length divided by its width. The soft lithography technique that was used achieved widths within 2-5 µm of the designed widths. Therefore, to distinguish devices designed to remove different amounts of fluid, the waste channel widths needed to differ by more than 5 µm. Ensuring this tolerance necessitated a waste channel length of 19 mm, which was fit compactly next to the spiral using a meander path (see FIG. 4).

Subsequently, to demonstrate a concentration increase of greater than an order of magnitude for separated and recovered particles, a device with a series of 6 waste channels was fabricated. This device was similar to the single waste channel devices except that it consisted of a 6-loop Archimedean spiral, six waste channels, and five branched outlets (FIG. 4). In this non-limiting example, each of the waste channels was 35 µm wide, 50 µm high, and 19 mm in long.

The goal of the SIFT device containing six waste channels and five outlets was to achieve fluid removal rates $r_Q$ larger than an order of magnitude. For W3-W6 $r_Q$ was 5, and for W1 and W2 $r_Q$ was 10. The five outlets, each having an $r_Q$ of 4, were used to further increase the amount of fluid separated from the recovered particles. Table 1 lists the $r_Q$ and the calculated fraction of fluid removed from the waste channels, $x_{s,j,calc}$, wherein the subscript "s" refers to secondary, or waste, channels.

The waste channel width, $w_{s,j,calc}$, required to achieve these $r_Q$ was calculated. To be able to use Equation (7), the $w_{s,j,calc}$ must be greater than h (50 µm); if not, the error from using the approximation was >10 µm. To achieve the desired fluid removal, $w_{s,j,calc}$ would be <h (50 µm), and so the full Equation (5) was solved to calculate $w_{s,j,calc}$ (see below for a discussion on using Equation (5) for w>h and w≈h). The $w_{s,j,calc}$ are listed in Table 1. With the exception of W2, they were within 4 µm of each other, and, as mentioned previously, fabrication tolerances were 2-5 µm. The waste channels were therefore all (including W2) made 35 µm wide ($w_{s,j,rev}$), where "rev" indicates revised parameters. This value was conservative to ensure that fabrication variations or expansion of the polydimethylsiloxane ("PDMS") microchannels (discussed below) would still result in channels that yielded the desired fluid removal. The width of the main channel following channels W3-W6, $w_{m,j-1,calc}$, was adjusted (reduced) to maintain $U_f$ and compensate for fluid removed from the main channel through the waste channels (described in more detail below). Using a 35 µm width for each of the waste channels and the $w_{m,j-1,calc}$, the fraction of fluid to be removed from the waste channels, $x_{s,j,rev}$, was determined (Table 1).

TABLE 1

List of parameters and dimensions for the multi-waste-channel spiral inertial filtration device shown in FIG. 4 (the standard deviation of five trials is indicated by ±).

| Channel | $r_Q$ | $x_{s,j,calc}$ | $x_{s,j,rev}$ | $x_{s,j,exp}$ | $w_{m,j-1,rev}$ (µm) | $w_{s,j,calc}$ (µm) | $w_{s,j,rev}$ (µm) |
|---|---|---|---|---|---|---|---|
| Inlet | — | — | — | — | 250 | — | — |
| W6 | 5 | 0.17 | 0.13 | 0.14 ± 0.010 | 210 | 41 | 35 |
| W5 | 5 | 0.17 | 0.13 | 0.18 ± 0.016 | 175 | 40 | 35 |
| W4 | 5 | 0.17 | 0.13 | 0.15 ± 0.006 | 145 | 40 | 35 |
| W3 | 5 | 0.17 | 0.13 | 0.16 ± 0.005 | 120 | 40 | 35 |
| W2 | 10 | 0.09 | 0.11 | 0.15 ± 0.003 | 110 | 32 | 35 |
| W1 | 10 | 0.09 | 0.08 | 0.12 ± 0.003 | 100 | 37 | 35 |
| O1 | 4 | 0.20 | 0.20 | 0.19 ± 0.010 | — | 75 | 75 |
| O2 | 4 | 0.20 | 0.20 | 0.21 ± 0.012 | — | 75 | 75 |
| O3 | 4 | 0.20 | 0.20 | 0.19 ± 0.029 | — | 75 | 75 |
| O4 | 4 | 0.20 | 0.20 | 0.20 ± 0.006 | — | 75 | 75 |
| O5 | 4 | 0.20 | 0.20 | 0.20 ± 0.008 | — | 75 | 75 |

The fractions of fluid collected experimentally from each waste channel and outlet, $x_{s,j,exp}$, are given in the 5$^{th}$ column of Table 1. The experimental values, $x_{s,j,exp}$, closely matched $x_{s,j,rev}$, differing by less than 5% in all cases. For a particle stream collected out of a single outlet, this would result in ~93% removal of fluid and a particle concentration factor of 13.

The devices were fabricated using standard soft lithography. A 10:1 mixture of polydimethylsiloxane (PDMS) prepolymer and curing agent (Sylgard 184, Dow Corning) was cast over a silicon master mold and cured at 50° C. for two hours. The master mold was formed by spin coating photoresist (Shipley 1813) onto a silicon wafer to a thickness of 3 µm, pre-baking for 1 min at 95° C., and exposing to 365 nm UV for 13 s. The photoresist was developed for 75 sec. in Microposit developer CD-30 (Shipley). The wafer was then etched at a rate of ~2 µm/min with deep reactive ion etching (DRIE) using the photoresist as the mask. The resist was stripped using Remover PG (MicroChem Corp.). To aid in the release of the cured PDMS, the silicon mold was silanized with trichloro(1H, 1H, 2H, 2H-perfluorooctyl) silane (Sigma Aldrich) using vapor deposition. Inlets and outlets were punched into the PDMS substrate, and it was sonicated in isopropanol for 90 min to remove PDMS debris and dust. The PDMS substrate was placed on an 85° C. hotplate for 2 hrs to remove the isopropanol and was then irreversibly bonded to glass using $O_2$ plasma (13 seconds at 0.75 Torr and 50 mW). Tygon tubing (0.02" I.D., 0.06" O.D.) was inserted into the inlet and outlets of the bonded devices.

Example 2: Fluid Removal Quantification

To determine the amount of fluid removed by the waste channels, deionized water was pumped into the devices at particular flow rates using a syringe pump (New Era Pump Systems, Inc.). To ensure that the flow rate had stabilized, each rate was held for 5 minutes. Fluid was then collected from the waste channels and the outlets for 5 min and the fluid was weighed to determine the volume collected. This was repeated three times for each flow rate for a single device.

Example 3: Particle Focusing

Figure 7:
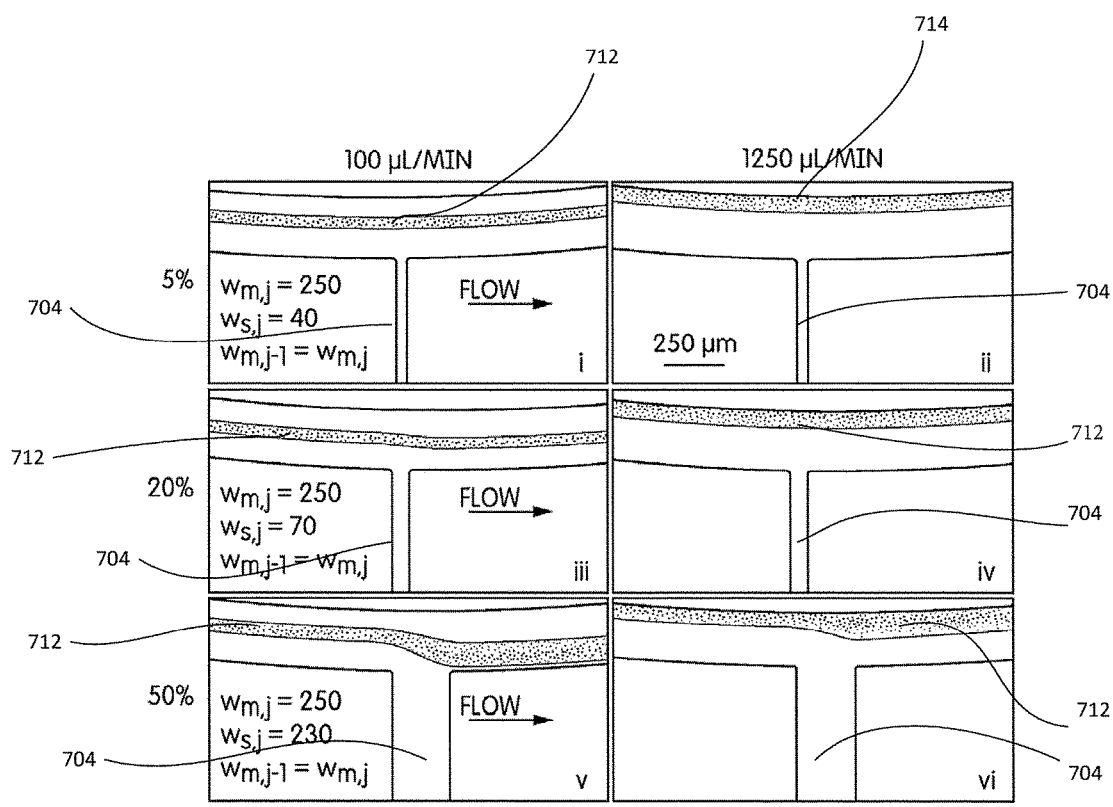
FIG. 7 represents images of 15 μm particles focused in SIFT devices having a single waste channel designed for 5% (i and ii), 20% (iii and iv), and 50% (v and vi) fluid removal at two flow rates (100 μL/min and 1250 μL/min).

FIG. 7 represents images of 15 µm particles focused in SIFT devices containing a single waste channel (704) designed for 5% (i and ii), 20% (iii and iv), and 50% (v and vi) fluid removal at two flow rates (100 µL/min and 1250 µL/min). The flow rates selected for experiment and verification are not intended to be limiting. Flow rates different from 100 µL/min or 1250 µL/min may be used and higher flow rates, e.g., up to 3 mL/min. may be employed. FIG. 7 showed that one can design for specific fluid removal rates; however, it is important to determine the impact of the fluid removal on the concentration and position of focused particle streams (712). Fluorescent particles 15 µm in diameter (14% coefficient of variation (CV)) (ThermoFisher Scientific) dispersed in deionized water at a concentration of 0.003% by weight were injected at increasing flow rates into the spiral inertial filtration devices containing a single waste channel (704) of varying width using the syringe pump. Images of the focused particles were taken using an inverted fluorescence microscope (Olympus Corporation, model IX51) equipped with a 12-bit digital CCD camera (Hamamatsu Photonics, model ORCA-03G). Three-second exposures were used to create visible particle traces. A sequence of 15 images was overlaid to create a composite image. To visualize the channel walls, a bright field image was taken, the image was inverted (converted to a negative) using Image) (U.S. National Institutes of Health), and the image was overlaid onto the particle focusing composite to create the final image.

At low fluid removal rates (5%), there was little effect on the focused particle stream (712) (FIGS. 7i and ii). With increasing flow rate, the particle stream moved from an equilibrium position near the center (FIG. 7i) to a new equilibrium position closer to the inner wall (714) (FIG. 7ii). This behavior was expected and was recently illustrated by Martel and Toner[51].

At a fluid removal rate of 20% (FIGS. 7iii and iv), there was a noticeable change of ~17 µm in the position of the focused particle stream (712) as it went past the waste channel (704). As fluid is removed, the average velocity in the channel $U_f$, along with De, decreases. For 100 µL/min (FIG. 7iii), $U_f$ decreased from 0.13 m/s to 0.11 m/s and De decreased from 0.79 to 0.63 after removal of 20% of the fluid. This was accompanied by an increase in the width of the particle stream (712) and a shift in the particle stream position. Previous reports have shown that the width of particle streams (712) in a spiral channel increases with decreases in $U_f$[51]. The position shift is likely due to distortions in the fluid streamlines caused by the large fluid removal rates, drawing the particle stream toward the waste channel. At the higher flow rate (FIG. 7iv), the impact of the waste channel (704) on the particle stream decreased because the particles occupied streamlines closer to the inner wall, which are less affected by the waste channel (704) (FIG. 7iv). In addition, as the streamlines are distorted, the width of the streamlines increases, causing a further increase in the width of the particle stream (710).

At 50% fluid removal (FIGS. 7v and vi), the shift in particle position and increase in particle stream width were exacerbated. At a flow rate of 100 µL/min (FIG. 7v), the distortion of the particle stream (~100 µm) caused some of the particles to be drawn out of the waste channel (704) (faint particles traces not easily visible in the figure). Even at high flow rates (FIG. 7vi), the particle stream (712) was affected by the fluid removal. Following the waste channel (704), the particle stream partially recovered because of the focusing nature of the spiral geometry; however, the large decrease in $U_f$ and De from 0.13 m/s to 0.07 m/s and 0.79 to 0.40, respectively, resulted in a wider particle stream that did not fully refocus. In practice, this limits the amount of fluid that can be removed from one waste channel without adversely affecting the results to ~20%. At higher fluid removal rates losses in recovery and separation efficiency will occur.

Channel Width Correction

To achieve high fluid removal rates without dispersing the particles as they pass the waste channels, at least one of $U_f$ and De must be maintained by modifying conditions of the main channel flow downstream of the waste channel. This can be most easily accomplished by changing the width of the main channel following the waste channel. However, $U_f$ and De have different dependences on the channel width and cannot be simultaneously corrected. As a result, the effect of correcting each individually was investigated to determine which parameter had the largest impact on focusing.

To maintain De, the width of the main channel following the $j^{th}$ waste channel, $w_{m,j-1}$, was calculated using $$\frac{w_{m,j-1} + h}{w_{m,j-1}^{1/3}} = \left(\frac{2 x_{m,j} Q_{m,j-1} \rho h^{1/2}}{\mu R^{1/2} De}\right)^{2/3}, \quad (10)$$

which was obtained by taking Equation (1) and substituting in Equation (2) and $U_{fmm,j-1} = x_{m,j} Q_{m,j-1} (w \cdot h)^{-1}$.

Figure 8A:
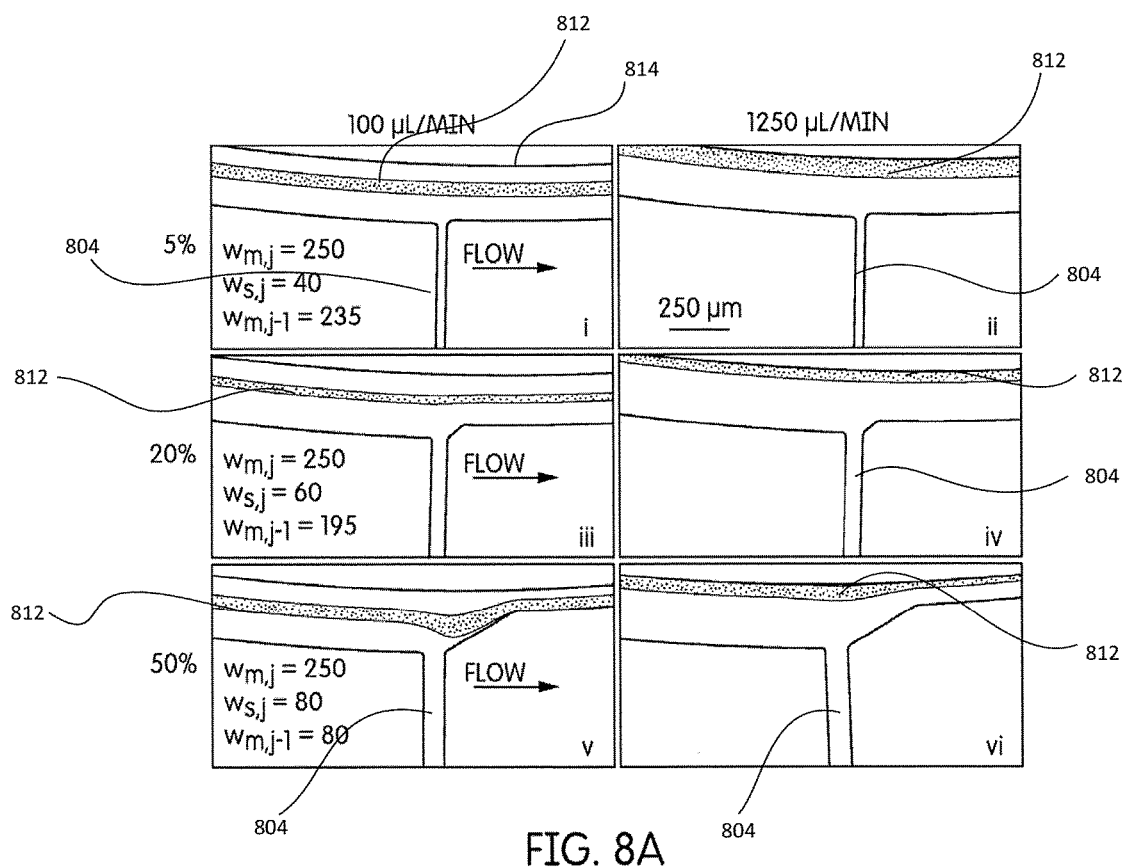
FIG. 8A represents particle focusing results for SIFT devices with the main channel widths corrected to maintain Dean number, De, following fluid removal from the main channel via a waste channel.

Devices with a single waste channel and corrected main channel widths for three removal rates were fabricated to experimentally confirm the prediction of Equation (10) on maintaining De. The downstream corners of the waste channels were filleted to allow for a gradual change to the corrected width of the main channel. Fluorescent particles of 15 µm diameter at a concentration of 0.003% were injected into the three devices. FIG. 8A represents particle focusing results for SIFT devices with the main channel widths corrected to maintain Dean number, De, following fluid removal from a single waste channel. FIG. 8A shows the particle stream (812) at fluid removal rates of 5, 20, and 50% at 100 µL/min and 1250 µL/min. As expected for a low fluid removal rate, at 5% there was no noticeable impact on the position or width of the particle stream (812) due to the presence of the waste channel (804) (See FIGS. 8Ai and ii). For low fluid removal rates, it is unnecessary to correct $w_{m,j-1}$ because De does not change significantly enough to impact particle focusing.

At 20% removal, the influence of the waste channel was effectively minimized by the width correction (compare FIGS. 8Aiii and iv with FIGS. 7iii and iv). For a flow rate of 1250 µL/min, the waste channel (804) had no impact on the particle stream (812) (See FIG. 8Aiv). At 100 µL/min, the particles maintained an almost fixed position relative to the inner wall (See FIG. 8Aiii), unlike the case without De correction, in which the particles shifted towards the waste channel (See FIG. 7iii). In fact, there was a minute shift (13 µm) of the particle stream (812) in FIG. 8Aiii toward the inner wall (814) as a result of the change in $w_{m,j-1}$. This occurs because changing $w_{m,j-1}$ to correct for De results in a different channel aspect ratio (w/h) following the waste channel (804). It has been shown that particle stream width and position depend on the aspect ratio; at a smaller aspect ratio particles occupy an equilibrium position closer to the inner wall.[51]

For 50% fluid removal, there was a sizeable distortion in the particle stream (812) at 100 µL/min (See FIG. 8Av). However, unlike for the uncorrected devices, particles did not exit the waste channel (804), and following the waste channel (804), the particle stream (812) refocused to a new equilibrium position. Again, the change in position of the focused stream can be explained by the change in aspect ratio: to correct for 50% fluid removal, $w_{m,j-1}$ was decreased from 250 µm to 80 µm, a change in the aspect ratio from 5 to 1.6. The normalized particle position, defined as the distance from the inner wall (814) over the total channel width, prior to the waste channel was 0.42, and after the waste channel it was 0.7. Unlike for the 20% fluid removal case (FIG. 8Aiii), the resulting shift in focusing position was towards the outer half of the channel. This behavior was unexpected, and the underlying physics is not yet known, but it was suspected that the initial particle position before the sudden large change in channel width plays a role. Such shifts could limit the amount of fluid removed using this strategy at the low flow rate of 100 µL/min. If a second waste channel removing a sizeable fraction of fluid were located further downstream, it is likely that the particle stream would be drawn out of the second waste channel (804). For 100 µL/min, this limits the fluid removal to ~50%, far short of the >90% desired. However, for 1250 µL/min the particle stream fully recovered after the waste channel. Again, the change in the aspect ratio had a noticeable effect on the particle stream, which, as expected, moved closer to the inner wall (814). At this speed, further removing fluid through downstream waste channels (804) is possible, allowing both higher fluid removal and greater particle concentration factors to be achieved simultaneously, a significant benefit of this designs.

One of the major limitations of adjusting channel width to maintain De is that as fluid is removed from sequential waste channels (FIG. 4) and $w_{m,j-1}$ is adjusted after each one, eventually the channel becomes too narrow to continue. Martel and Toner[51] showed that as the aspect ratio (w/h) approaches unity, particle confinement, defined as the ratio of the channel width to the particle stream width, decreases. If the particle streams occupy a larger fraction of the channel, particles of different sizes come into close proximity or even overlap, making separation difficult.

The approach of correcting the width to maintain the fluid velocity, $U_f$, was tested to determine if this provides an advantage as compared to correction for De. In this case, the new width depends only on the fraction of fluid remaining in the main channel, $x_{m,j-1}$, and the width of the previous section of main channel, $w_{m,j}$:

$$w_{m,j-1} = x_{m,j-1} w_{m,j} \quad (11)$$

Figure 8B:
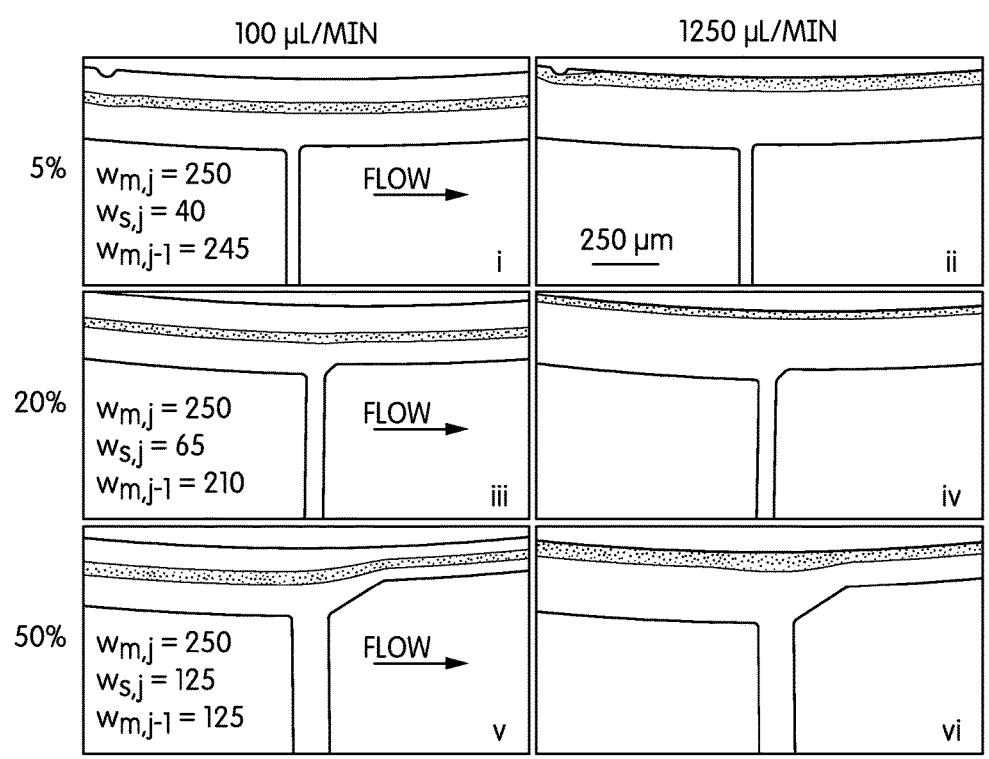
FIG. 8B represents particle focusing results for SIFT devices with the main channel widths corrected to maintain average fluid velocity, $U_f$, following fluid removal from the main channel via a waste channel.

FIG. 8B shows the results of focusing 15 µm fluorescent particles in devices designed to maintain fluid velocity, $U_f$, following fluid removal from a single waste channel. The waste channel had little to no effect on the particle stream for 5% removal (See FIGS. 8Bi and ii) and 20% removal (See FIGS. 8Biii and iv). The results were similar to those obtained for maintaining De (compare FIGS. 8Ai, ii, iii, iv) because $w_{m,j-1}$ corrected for De and $U_f$ for 5% removal and 20% removal differed by only 4% and 7%, respectively. For 50% fluid removal, the $w_{m,j-1}$ was 36% larger for the $U_f$ correction than for the De correction. At the 100 µL/min flow rate, the particle stream recovered in both cases but to different equilibrium positions (compare FIGS. 8Av and 7v), and at 1250 µL/min the two results were nearly indistinguishable, even though the De in FIG. 8Avi is 9.87 following the waste channel and in FIG. 8Bvi it is 7.83.

FIG. 8 shows that correcting for either De or $U_f$ eliminated particle loss through the waste channel (804) and improved focusing after the waste channel (804). However, there are advantages to the $U_f$ correction. For low flow rates (100 µL/min), $U_f$ correction prevented particle stream dispersion at the waste channel (FIG. 8B). The particle stream (812) maintained its trajectory at a normalized particle position of 0.45. In addition, since the corrected width for $U_f$ is wider than for De, more fluid can be removed from sequential waste channels without negatively affecting particle focusing and separation.

In an alternate embodiment, the main channel (802) of the device may have a non-uniform height varying along the length of the main channel (802) so that the channel geometry could be varied to maintain a substantially constant De or $U_f$ by varying the height instead of, or in addition to, varying the width. In one such alternate embodiment having more than one secondary channel, the height of the main channel is substantially constant between each two neighboring secondary channels.

Other corrections that could be made to sustain particle focusing after fluid removal, other than, or in addition, to De and $U_f$, by modifying the geometry of the main channel 1250 (e.g., height and/or width) are for Reynolds number and particle Reynolds number.

To evaluate particle separation from a fluid stream containing particles of more than one particle size, 4.8 µm (5% CV) (Duke Scientific Corp.) and 8 µm (18% CV) (Thermo-Fisher Scientific) fluorescent particles dispersed in deionized water at a concentration of 0.001% by weight were injected into the multi-waste-channel SIFT device (FIG. 4) at a flow rate of 950 µL/min. The flow was allowed to equilibrate for 5 minutes. Fluid was collected from the waste channels (804) and the outlets into vials for 5 minutes. Particles in each vial were counted using a hemocytometer (INCYTO). The separation was repeated five times with two devices (n=3 in one device and n=2 in the second device).

Figure 9A:
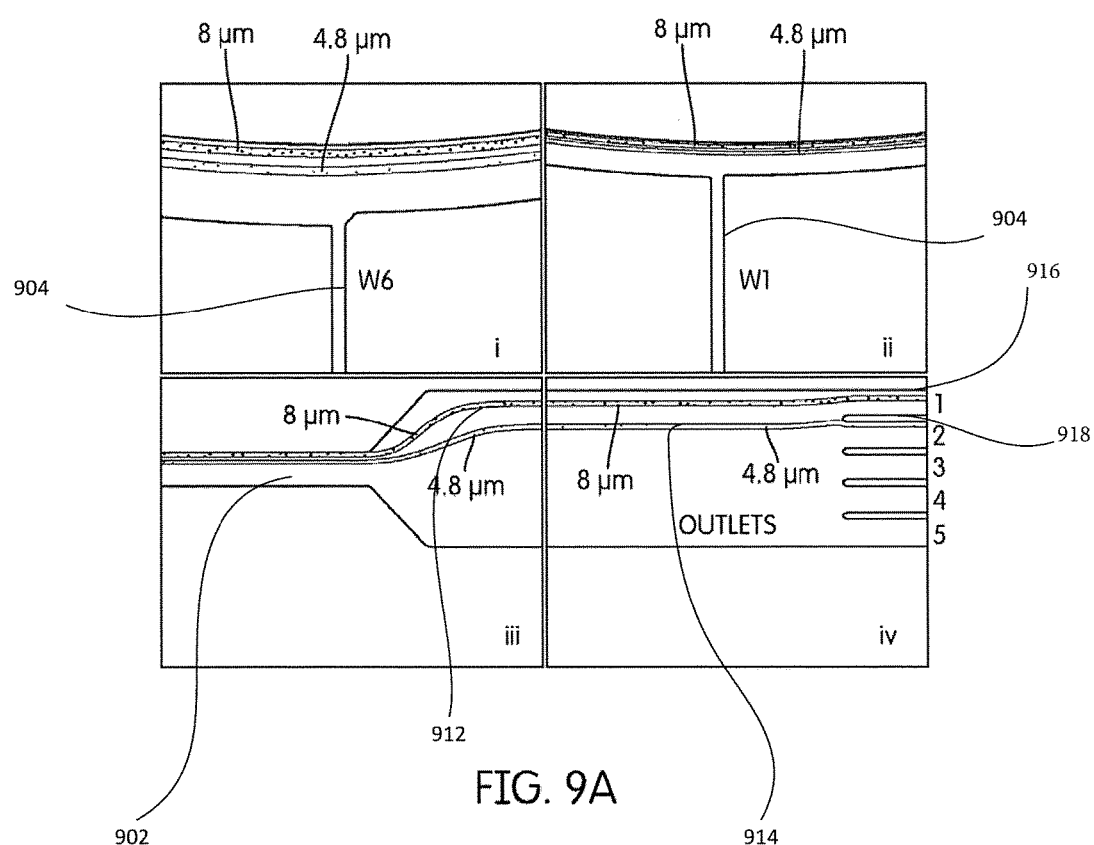
FIG. 9A represents fluorescent images showing the separation of two particle sizes, 4.8 μm and 8 μm, in a SIFT device designed for removal of 93% of the inlet fluid.
Figure 9B:
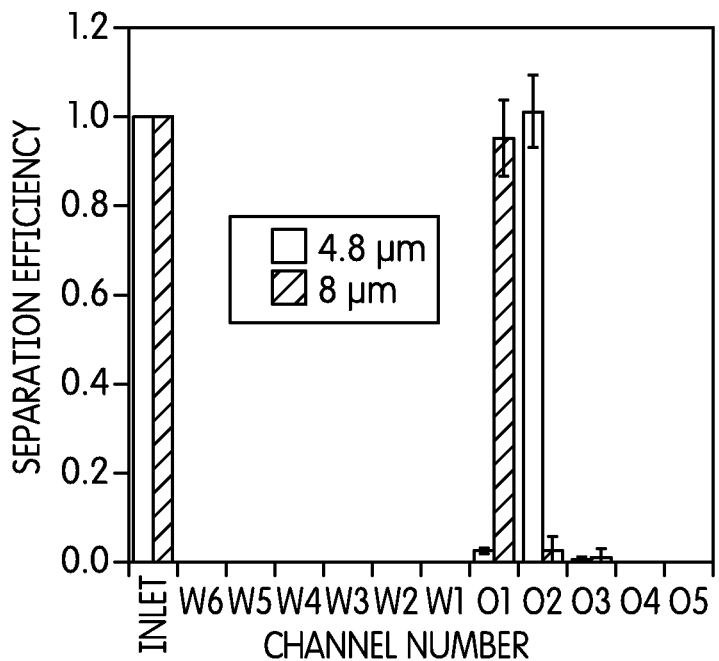
FIG. 9B is a graph of separation efficiency, calculated as the number of particles collected at each outlet O1-O5 or waste channel W1-W6, over the number input into the device.
Figure 9C:
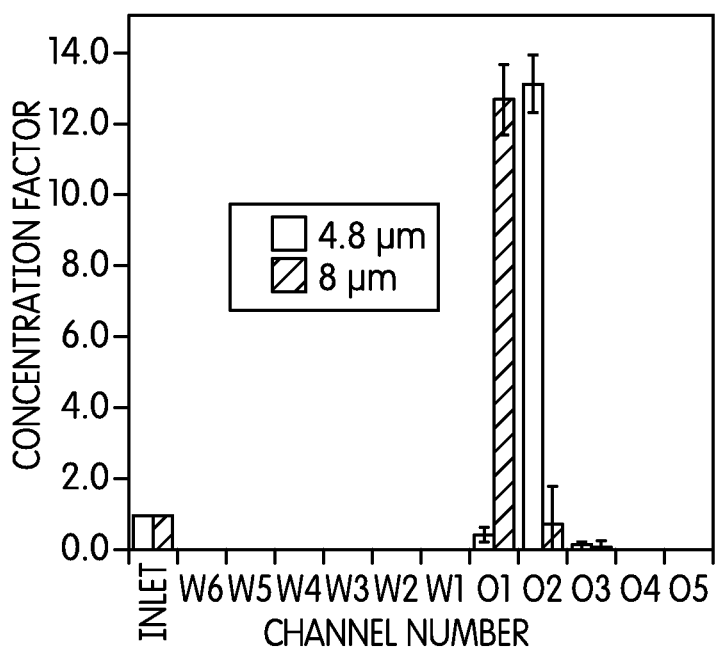
FIG. 9C is a graph of particle concentration factor (concentration at each outlet or waste channel, assuming 100% recovery, over the inlet concentration multiplied by the separation efficiency).

These results are shown in FIGS. 9A-9C. FIG. 9A represents fluorescent images showing the separation of two particle sizes, 4.8 µm and 8 µm, in a SIFT device designed for removal of 93% of the inlet fluid. The two particle sizes were completely separated at W6 (FIG. 9Ai). Because of the main channel width correction (main channel width after the waste channel is smaller than before the waste channel), the particle streams (912) and (914) were not impacted by the waste channels (904). Even at W1, where 63% of the inlet fluid was removed, there was no noticeable impact on the particle streams (912) and (914) (FIG. 9Aii). Due to the change in the aspect ratio and the decreased particle confinement, the separation between the two particle streams (912) and (914) decreased, but the two sizes were still clearly separated. The channel (902) was expanded (FIG. 9Aiii) to allow for the two particle streams to be separated into different outlets, with the 8 µm (red) particles flowing out of O1 (916) and the 4.8 µm particles out of O2 (918) (FIG. 9Aiv).

FIG. 9B is a graph of separation efficiency, calculated as the number of particles collected at each outlet over the number input into the device. Error bars are standard deviations from 5 experiments in two devices (n=3 in one device and n=2 in the other). A separation efficiency of 100.4±6.2 and 95.2±9.9 was achieved for the 4.8 µm and 8 µm particles, respectively. (The separation efficiency greater than 100% is attributed to errors associated with particle counting using a hemocytometer.) FIG. 9C is a graph of particle concentration factor (concentration at each outlet, assuming 100% recovery, over the inlet concentration multiplied by the separation efficiency). Again, error bars are standard deviations from 5 experiments in two devices (n=3 in one device and n=2 in the other). Since each particle stream was separated into a different outlet, the total fluid removed for each particle size was ~93%, which corresponded to a concentration factor of 13.4±0.82 for the 4.8 µm particles and 12.7±0.99 for the 8 µm particles (FIG. 9C).

Figure 12:
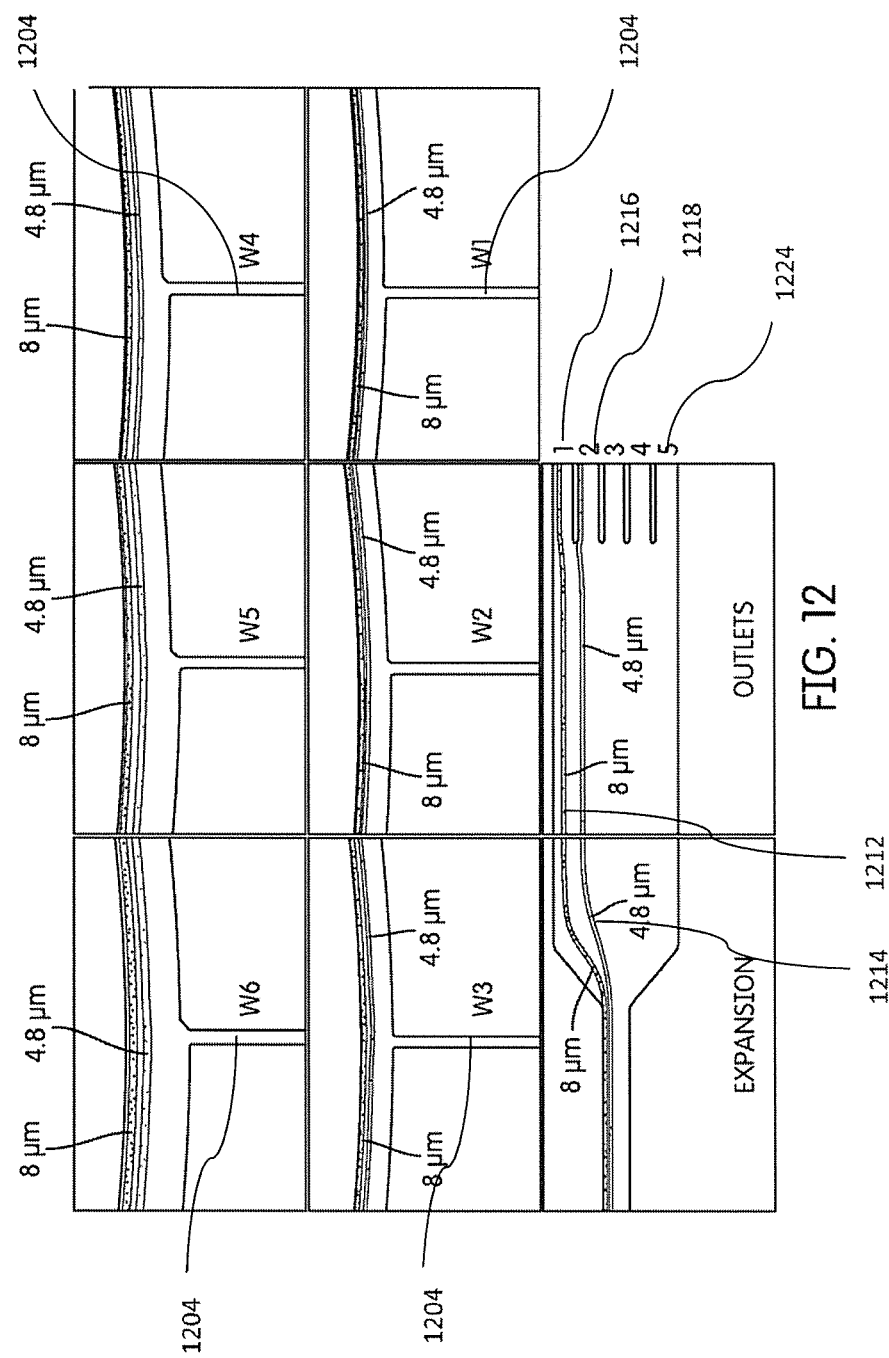
FIG. 12 represents fluorescent images showing the separation into particle streams of two particle sizes, 4.8 μm (bottom) and 8 μm (top), in a SIFT device designed for removal of 93% of the inlet fluid.

Streams (1212) and (1214) of two particle sizes, 4.8 µm and 8 µm, in a spiral inertial filtration (SIFT) device containing 6 waste channels (1204) and five outlets (1216)-(1224) are shown in FIG. 12 at each waste channel (1204) WI-W6 and at the outlets (1216)-(1224), 1-5. The particle streams are clearly separated at every location.

Derivation of Waste Channel Resistance Equation (4)

Figure 10:
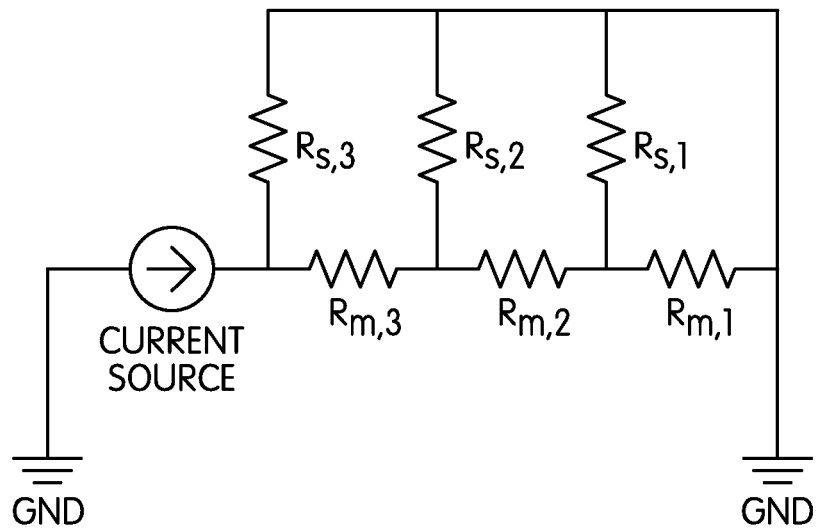
FIG. 10 is a diagram of an equivalent circuit for a device with three waste channels having resistances $R_s$ and a main channel with three segments of resistance $R_m$.

To simplify the derivation, an illustration is provided using a device with three waste channels. The equivalent circuit is shown in FIG. 10. Note that the numbering is from back to front, so "first" means "first from the end". The constant flow rate produced by the syringe pump is modeled as a current source.

The derivation begins with the resistance of the first (right-most in FIG. 9A) leg of the main channel $R_{m,1}$ and the resistance of the first side waste channel, $R_{s,1}$. Using an equivalent circuit analogy, in which the pressure drop $\Delta P$ is like a voltage and the fluid flow Q is like current, it is possible to write expressions analogous to Ohm's law (V=IR) for pressure-driven flow, known as Hagen-Poiseuille's law ($\Delta P = QR$):

$$\Delta P_{s,1} = Q_{s,1} R_{s,1} \tag{13}$$

$$\Delta P_{m,1} = Q_{m,1} R_{m,1} \tag{14}$$

where $\Delta P_{s,1}$ and $\Delta P_{m,1}$ are the pressure drops in the waste channel and the main channel, respectively, and $Q_{s,1}$ and $Q_{m,1}$ are the corresponding volumetric flow rates, respectively. (See Oh et al.[75] for an excellent review of fluidic equivalent circuits with numerous examples). $\Delta P_{s,1} = \Delta P_{m,1}$ because they both start at the same point, and thus have the same pressure on their left sides, and both end at the same point, which is atmospheric pressure (or ground) on their right sides. Defining $r_{Q,J}$ as the volumetric flow ratio between this main and secondary channel, $$R_{Q,1} = Q_{m,1} / Q_{s,1} \tag{15}$$

Equations (13), (14), and (15) are combined to yield the hydraulic resistance of the first waste channel, $R_{s,1}$:

$$R_{s,1} = r_{Q,1} R_{m,1}, \tag{16}$$

Similarly, $\Delta P_{s,2}$ for the second waste channel, which also connects to ground, is $$\Delta P_{s,2} = Q_{s,2} R_{s,2} \tag{17}$$

Figure 11:
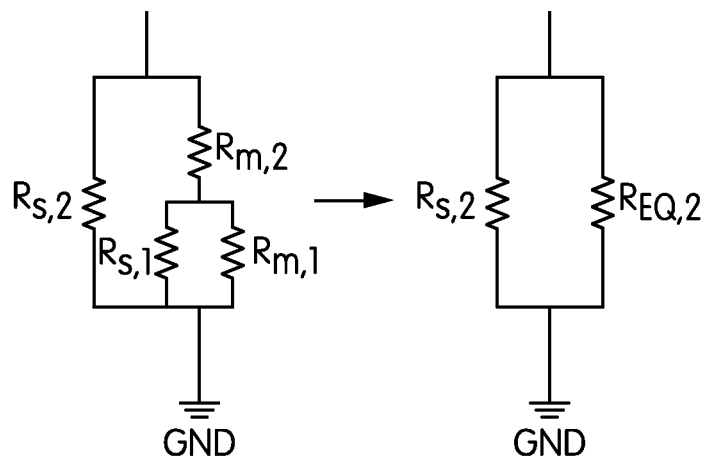
FIG. 11 is a diagram of an equivalent resistance $R_{EQ,2}$ that replaces $R_{m,2}$, $R_{m,1}$, and $R_{s,1}$.

However, to determine the resistance of the second main channel, $R_{m,2}$, a different approach is needed. The pressure drop $\Delta P_{m,2}$ is not known (it does not terminate at atmospheric pressure), and so $R_{m,2}$ cannot be obtained directly. To find it, an equivalent resistance, $R_{EQ,2}$, across the combination of the second main channel segment and the first two channels is defined, incorporating $R_{m,2}$, $R_{m,1}$, and $R_{s,1}$:

$$R_{EQ,2} = R_{m,2} + \frac{1}{\frac{1}{R_{s,1}} + \frac{1}{R_{m,1}}} \tag{18}$$

where $R_{m,1}$ and $R_{s,1}$ are in parallel and $R_{m,2}$ is in series (FIG. 11).

Inserting Equation (16) into Equation (18) and rearranging yields $$R_{EQ,2} = R_{m,2} + \frac{R_{s,1}}{1 + r_{Q,1}}. \tag{19}$$

The pressure drop across $R_{EQ,2}$ is $$\Delta P_{EQm,2} = \Delta P_{s,2} \tag{20}$$

where $Q_{m,2}$ is the volumetric flow rate of the second main channel, and since $\Delta P_{EQm,2}$ and $\Delta P_{s,2}$ start at the same node and both terminate at ground, then $$\Delta P_{EQm,2} = \Delta P_{s,2}. \tag{21}$$

Combining Equation (17), (19), (20), and (21) and defining a volumetric flow ratio of $r_{Q,2} = Q_{m,2}/Q_{s,2}$ gives $$R_{s,2} = r_{Q,2}\left[R_{m,2} + \frac{R_{s,1}}{1 + r_{Q,1}}\right]. \tag{22}$$

The resistance of the third side waste channel, $R_{s,3}$, is found in the same manner. The pressure drop across $R_{s,3}$ is $$\Delta P_{s,3} = Q_{s,3} R_{s,3} \tag{23}$$

Again, the pressure drop across the third main channel, $\Delta P_{m,3}$, is unknown and so an equivalent pressure, $\Delta P_{EQm,3}$, is defined as $$\Delta P_{EQm,3} = Q_{m,3} R_{EQ,3} \tag{24}$$

where $R_{EQ,3}$ is the equivalent resistance and is given by $$R_{EQ,3} = R_{m,3} + \frac{1}{\frac{1}{R_{s,2}} + \frac{1}{R_{EQ,2}}} = R_{m,3} + \frac{1}{\frac{1}{R_{s,2}} + \frac{1}{R_{m,2} + \frac{R_{s,1}}{1 + r_{Q,1}}}}. \tag{25}$$

From Equation (22) it can be seen that $$\frac{R_{s,2}}{r_{Q,2}} = R_{m,2} + \frac{R_{s,1}}{1 + r_{Q,1}}, \tag{26}$$

so Equation (24) can be rewritten as $$R_{EQ,3} = R_{m,3} + \frac{R_{s,2}}{1 + r_{Q,2}}. \tag{27}$$

Again $\Delta P_{s,3} = \Delta P_{EQm,3}$. Combining Equations (23), (24), and (27) and defining $r_{Q,3} = Q_{m,3}/Q_{s,3}$ gives $$R_{s,3} = r_{Q,3}\left[R_{m,3} + \frac{R_{s,2}}{1 + r_{Q,2}}\right]. \tag{28}$$

Equations (22) and (28) can be written in the general form $$R_{s,j} = r_{Q,j}\left[R_{m,j} + \frac{R_{s,j-1}}{1 + r_{Q,j-1}}\right] \tag{29}$$

shown in Equation (4) for j=2, 3, 4, . . . , n−1, n.

Hydraulic Resistance.

For Equation (5) to be valid, the width of the channel, w, must be greater than the height, h. As previously discussed, for some cases Equation (5) can be simplified to Equation (7). Whether Equation (7) is valid will depend on the specific parameters of the system.

For w<h, a variation of Equation (5) can be used. The hydraulic resistance of a rectangular channel depends on its cross-sectional area, so the resistance of a rectangular channel with dimensions w×h is the same as that of a channel with "w" and "h" reversed. In other words, rotating a rectangular channel by 90° does not change its resistance. To determine the hydraulic resistance of a channel with w<h, one can therefore rewrite Equation (5) with w and h reversed, as $$R_H = \frac{12\mu L}{hw^3}\left(1 - \frac{192w}{\pi^5 h}\sum_{n=1,3,5,...}^{\infty}\frac{\tanh\left(\frac{n\pi h}{2w}\right)}{n^5}\right)^{-1}. \quad (30)$$

A study for h=50 μm, L=19 mm, n=1, and μ=10$^{-3}$ Pa s$^{-1}$ was performed to determine the thresholds at which Equation (5), Equation (7), and Equation (30) could be used for widths w ranging from 10 μm to 200 μm (i.e. aspect ratios ranging from 0.2 to 4). The results are shown in Table 2.

TABLE 2

Hydraulic resistance calculated using three different equations for various w and with h = 50 μm. Results within 10% are highlighted.

| Width, w (μm) | Aspect Ratio (w/h) | Hydraulic Resistance, $R_H$ (Pa m$^3$ s$^{-1}$) | | | Difference from Eq. (5) (%) | |
|---|---|---|---|---|---|---|
| | | Eq. (5) | Eq. (7) | Eq. (29) | Eq. (7) approximation | Eq. (30) w ↔ h |
| 10 | 0.2 | 3.99 × 10$^{15}$ | NA* | 5.21 × 10$^{15}$ | — | 30.52 |
| 25 | 0.5 | 4.12 × 10$^{14}$ | NA* | 4.25 × 10$^{14}$ | — | 3.04 |
| 30 | 0.6 | 2.64 × 10$^{14}$ | NA* | 2.69 × 10$^{14}$ | — | 1.81 |
| 35 | 0.7 | 1.84 × 10$^{14}$ | 5.21 × 10$^{14}$ | 1.86 × 10$^{14}$ | 182.65 | 1.10 |
| 40 | 0.8 | 1.37 × 10$^{14}$ | 2.15 × 10$^{14}$ | 1.38 × 10$^{14}$ | 56.83 | 0.63 |
| 45 | 0.9 | 1.06 × 10$^{14}$ | 1.35 × 10$^{14}$ | 1.07 × 10$^{14}$ | 26.92 | 0.29 |
| 50 | 1.0 | 8.59 × 10$^{13}$ | 9.86 × 10$^{13}$ | 8.59 × 10$^{13}$ | 14.75 | 0.00 |
| 55 | 1.1 | 7.14 × 10$^{13}$ | 7.76 × 10$^{13}$ | 7.12 × 10$^{13}$ | 8.72 | 0.26 |
| 60 | 1.2 | 6.07 × 10$^{13}$ | 6.40 × 10$^{13}$ | 6.04 × 10$^{13}$ | 5.42 | 0.50 |
| 65 | 1.3 | 5.26 × 10$^{13}$ | 5.44 × 10$^{13}$ | 5.22 × 10$^{13}$ | 3.49 | 0.75 |
| 70 | 1.4 | 4.63 × 10$^{13}$ | 4.74 × 10$^{13}$ | 4.58 × 10$^{13}$ | 2.32 | 1.01 |
| 75 | 1.5 | 4.13 × 10$^{13}$ | 4.19 × 10$^{13}$ | 4.07 × 10$^{13}$ | 1.58 | 1.28 |
| 80 | 1.6 | 3.72 × 10$^{13}$ | 3.76 × 10$^{13}$ | 3.66 × 10$^{13}$ | 1.11 | 1.57 |
| 85 | 1.7 | 3.38 × 10$^{13}$ | 3.41 × 10$^{13}$ | 3.32 × 10$^{13}$ | 0.80 | 1.88 |
| 90 | 1.8 | 3.10 × 10$^{13}$ | 3.12 × 10$^{13}$ | 3.03 × 10$^{13}$ | 0.60 | 2.22 |
| 95 | 1.9 | 2.86 × 10$^{13}$ | 2.87 × 10$^{13}$ | 2.79 × 10$^{13}$ | 0.46 | 2.57 |
| 100 | 2.0 | 2.65 × 10$^{13}$ | 2.66 × 10$^{13}$ | 2.57 × 10$^{13}$ | 0.36 | 2.95 |
| 200 | 4.0 | 1.08 × 10$^{-13}$ | 1.08 × 10$^{-13}$ | 9.17 × 10$^{12}$ | 0.08 | 15.26 |

NA indicates that the calculated resistance was negative.

For the parameters used here, Equation (7) was a good approximation for all aspect ratios w/h>1 (w>50 μm): the percent difference was less than 10%. Above w/h=1.6, the percent difference was less than 1%. As expected, using the simplified Equation (7) for w/h≤1 introduced error, with the magnitude of the error increasing strongly as w/h decreased.

Interestingly, the error associated with using Equation (5) instead of Equation (29) was small even for w<h until w/h<0.5. For w/h=2 to 0.5, Equations (5) and (29) differed by less than 3%, so they could be used interchangeably. In other words, for w≈h both Equation (5) and Equation (29) were valid. Beyond these aspect ratios, the correct equation, either Equation (5) or Equation (29) must be used.

Techniques that can quickly process large sample volumes while achieving efficient recovery and enrichment of rare particles are necessary for lab-on-a-chip (LOC) applications that require a large volume reduction in order to enable subsequent microfluidic processing steps. In this work, a spiral inertial filtration (SIFT) device capable of achieving particle concentration factors of 13× (removal of 93% of the inlet fluid) at ~1 mL/min was presented. The amount of fluid removed was accurately controlled by designing a device with the fluidic resistances precisely balanced between the main flow channel and the waste channels. By ensuring that the fluid velocity in the main channel was maintained following each fluid removal, removal of large fractions of the inlet fluid was possible without disrupting the focused particle streams, yielding nearly 100% separation efficiency.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

1. J. D. Adams, U. Kim, and H. T. Soh, Proceedings of the National Academy of Sciences of the United States of America, 2008, 105, 18165-70.
2. A. Alazzam, I. Stiharu, R. Bhat, and A.-N. Meguerditchian, Electrophoresis, 2011, 32, 1327-36.
3. J. P. Beech, P. Jonsson, and J. O. Tegenfeldt, Lab on a Chip, 2009, 9, 2698-706.
4. S. Choi, J. M. Karp, and R. Karnik, Lab on a Chip, 2012, 12, 1427-30.
5. J. A. Davis, D. W. Inglis, K. J. Morton, D. A. Lawrence, L. R. Huang, S. Y. Chou, J. C. Sturm, and R. H. Austin, Proceedings of the National Academy of Sciences of the United States of America, 2006, 103, 14779-84.
6. I. Doh and Y. Cho, Sensors and Actuators A: Physical, 2005, 121, 59-65.
7. T. P. Forbes and S. P. Forry, Lab on a Chip, 2012, 12, 1471-9.
8. K.-H. Han and a B. Frazier, Lab on a Chip, 2008, 8, 1079-86.
9. C.-H. Hsu, D. Di Carlo, C. Chen, D. Irimia, and M. Toner, Lab on a Chip, 2008, 8, 2128-34.
10. L. R. Huang, E. C. Cox, R. H. Austin, and J. C. Sturm, Science, 2004, 304, 987-90.
11. D. W. Inglis, M. Lord, and R. E. Nordon, Journal of Micromechanics and Microengineering, 2011, 21, 054024.
12. U. Kim, J. Qian, S. a Kenrick, P. S. Daugherty, and H. T. Soh, Analytical Chemistry, 2008, 80, 8656-61.
13. P. B. Lillehoj, H. Tsutsui, B. Valamehr, H. Wu, and C.-M. Ho, Lab on a Chip, 2010, 10, 1678-82.
14. W. Mao and A. Alexeev, Physics of Fluids, 2011, 23, 051704.
15. H.-S. Moon, K. Kwon, S.-I. Kim, H. Han, J. Sohn, S. Lee, and H.-I. Jung, Lab on a Chip, 2011, 11, 1118-25.
16. F. Petersson, L. Aberg, A.-M. Sward-Nilsson, and T. Laurell, Analytical Chemistry, 2007, 79, 5117-23.

17. J. Takagi, M. Yamada, M. Yasuda, and M. Seki, Lab on a Chip, 2005, 5, 778-84.
18. M. Urdaneta and E. Smela, Journal of Micromechanics and Microengineering, 2008, 18, 015001.
19. H. Wei, B.-H. Chueh, H. Wu, E. W. Hall, C.-W. Li, R. Schirhagl, J.-M. Lin, and R. N. Zare, Lab on a Chip, 2010, 238-245.
20. M. Yamada and M. Seki, Lab on a Chip, 2005, 5, 1233-9.
21. A. J. Mach and D. Di Carlo, Biotechnology and Bioengineering, 2010, 107, 302-311.
22. X. Cheng, D. Irimia, M. Dixon, K. Sekine, U. Demirci, L. Zamir, R. G. Tompkins, W. Rodriguez, and M. Toner, Lab on a chip, 2007, 7, 170-8.
23. S. C. Hur, A. J. Mach, and D. Di Carlo, Biomicrofluidics, 2011, 5, 022206.
24. S. L. Stott, C.-H. Hsu, D. I. Tsukrov, M. Yu, D. T. Miyamoto, B. a Waltman, S. M. Rothenberg, A. M. Shah, M. E. Smas, G. K. Korir, F. P. Floyd, A. J. Gilman, J. B. Lord, D. Winokur, S. Springer, D. Irimia, S. Nagrath, L. V. Sequist, R. J. Lee, K. J. Isselbacher, S. Maheswaran, D. a Haber, and M. Toner, Proceedings of the National Academy of Sciences of the United States of America, 2010, 107, 18392-7.
25. D. Di Carlo, Lab on a Chip, 2009, 9, 3038-46.
26. A. A. S. Bhagat, S. S. Kuntaegowdanahalli, and I. Papautsky, Microfluidics and Nanofluidics, 2008, 7, 217-226.
27. A. A. S. Bhagat, S. S. Kuntaegowdanahalli, and I. Papautsky, Physics of Fluids, 2008, 20, 101702.
28. G. Segre and A. Silberberg, Nature, 1961, 189, 209-210.
29. A. A. S. Bhagat, H. W. Hou, L. D. Li, C. T. Lim, and J. Han, Lab on a Chip, 2011, 1870-1878.
30. S. C. Hur, H. T. K. Tse, and D. Di Carlo, Lab on a Chip, 2010, 10, 274-80.
31. M. G. Lee, S. Choi, and J.-K. Park, Journal of Chromatography A, 2010, 1218, 4138-4143.
32. M. G. Lee, S. Choi, H.-J. Kim, H. K. Lim, J.-H. Kim, N. Huh, and J.-K. Park, Applied Physics Letters, 2011, 98, 253702.
33. A. J. Mach, J. H. Kim, A. Arshi, S. C. Hur, and D. Di Carlo, Lab on a Chip, 2011.
34. J.-S. Park, S.-H. Song, and H.-I. Jung, Lab on a Chip, 2009, 9, 939.
35. H. a Nieuwstadt, R. Seda, D. S. Li, J. B. Fowlkes, and J. L. Bull, Biomedical Microdevices, 2011, 13, 97-105.
36. T. Tanaka, T. Ishikawa, K. Numayama-Tsuruta, Y. Imai, H. Ueno, T. Yoshimoto, N. Matsuki, and T. Yamaguchi, Biomedical Microdevices, 2011.
37. Z. Wu, B. Willing, J. Bjerketorp, J. K. Jansson, and K. Hjort, Lab on a Chip, 2009, 9, 1193-9.
38. C. Blattert, R. Jurischka, I. Tahhan, A. Schoth, P. Kerth, and W. Menz, The 26th Annual International Conference of the IEEE Engineering in Medicine and Biology Society, 2004, 4, 2627-30.
39. B. H. Kwon, H. H. Kim, J. Cha, C. H. Ahn, T. Arakawa, S. Shoji, and J. S. Go, Japanese Journal of Applied Physics, 2011, 50, 097301.
40. S. Ookawara, D. Street, and K. Ogawa, Chemical Engineering Science, 2006, 61, 3714-3724.
41. N. Oozeki, S. Ookawara, K. Ogawa, P. Lob, and V. Hessel, AIChE Journal, 2009, 55, 24-34.
42. E. Sollier, H. Rostaing, P. Pouteau, Y. Fouillet, and J.-L. Achard, Sensors and Actuators B: Chemical, 2009, 141, 617-624.
43. D. H. Yoon, J. B. Ha, Y. K. Bahk, T. Arakawa, S. Shoji, and J. S. Go, Lab on a Chip, 2009, 9, 87-90.
44. D. Di Carlo, J. F. Edd, D. Irimia, R. G. Tompkins, and M. Toner, Analytical chemistry, 2008, 80, 2204-11.
45. D. Di Carlo, D. Irimia, R. G. Tompkins, and M. Toner, Proceedings of the National Academy of Sciences of the United States of America, 2007, 104, 18892-7.
46. J. Oakey, R. W. Applegate, E. Arellano, D. Di Carlo, S. W. Graves, and M. Toner, Analytical Chemistry, 2010, 82, 3862-7.
47. A. A. S. Bhagat, S. S. Kuntaegowdanahalli, and I. Papautsky, Lab on a Chip, 2008, 8, 1906-14.
48. I. Gregoratto, C. J. McNeil, and M. W. Reeks, in Proceedings of SPIE 6465, 2007, p. 646503.
49. S. S. Kuntaegowdanahalli, A. A. S. Bhagat, G. Kumar, and I. Papautsky, Lab on a Chip, 2009, 9, 2973-80.
50. W. C. Lee, A. A. S. Bhagat, S. Huang, K. J. Van Vliet, J. Han, and C. T. Lim, Lab on a Chip, 2011, 1359-1367.
51. J. M. Martel and M. Toner, Physics of Fluids, 2012, 24, 032001.
52. J. Seo, M. H. Lean, and A. Kole, Applied Physics Letters, 2007, 91, 033901.
53. J. Seo, M. H. Lean, and A. Kole, Journal of Chromatography A, 2007, 1162, 126-31.
54. A. Russom, A. K. Gupta, S. Nagrath, D. Di Carlo, J. F. Edd, and M. Toner, New journal of physics, 2009, 11, 75025.
55. J. Wang, Y. Zhan, V. M. Ugaz, and C. Lu, Lab on a Chip, 2010, 10, 2057-61.
56. A. A. S. Bhagat, S. S. Kuntaegowdanahalli, N. Kaval, C. J. Seliskar, and I. Papautsky, Biomedical Microdevices, 2010, 12, 187-95.
57. A. P. Sudarsan and V. M. Ugaz, Proceedings of the National Academy of Sciences of the United States of America, 2006, 103, 7228-7223.
58. S. Berger, Annual Review of Fluid Mechanics, 1983, 15, 461-512.
59. J. Sun, M. Li, C. Liu, Y. Zhang, D. Liu, W. Liu, G. Hu, and X. Jiang, Lab on a Chip, 2012, DOI: 10.1039/c21c40679a.
60. S. Yang, A. Undar, and J. D. Zahn, Lab on a Chip, 2006, 6, 871-80.
61. S. Yang, A. Undar, and J. D. Zahn, ASAIO Journal, 2005, 51, 585-590.
62. R. D. Jaggi, R. Sandoz, and C. S. Effenhauser, Microfluidics and Nanofluidics, 2006, 3, 47-53.
63. S. S. Shevkoplyas, T. Yoshida, L. L. Munn, and M. W. Bitensky, Analytical Chemistry, 2005, 77, 933-7.
64. X. Xue, M. K. Patel, M. Kersaudy-Kerhoas, C. Bailey, and M. P. Y. Desmulliez, Computer Methods in Biomechanics and Biomedical Engineering, 2011, 14, 549-60.
65. E. Sollier, M. Cubizolles, Y. Fouillet, and J.-L. Achard, Biomedical Microdevices, 2010, 12, 485-97.
66. Z. Geng, Z. Xu, W. Wang, W. Su, and Z. Li, in Solid-State and Integrated Circuit Technology (ICSICT), 2010 10th IEEE International Conference on, IEEE, 2010, pp. 1474-1476.
67. Y. Ju, Z. Geng, L. Zhang, W. Wang, and Z. Li, in 2011 16th International Solid State Sensors Acutators and Microsystems conference, IEEE, 2011, pp. 298-301.
68. H. Maruyama, S. Sakuma, Y. Yamanishi, and F. Arai, in 2009 IEEE/SICE International Symposium on System Integration (SII), IEEE, 2009, pp. 7-12.
69. T. Tanaka, T. Ishikawa, K. Numayama-Tsuruta, and Y. Imai, Lab on a Chip, 2012, DOI: 10.1039/C2LC40354D.
70. H.-C. Tseng, R. Wu, H.-Y. Chang, and F.-G. Tseng, in Micro Electro Mechanical Systems (MEMS), 2012 IEEE 25th International Conference on, Paris, France, pp. 835-838.

71. K. W. Oh, K. Lee, B. Ahn, and E. P. Furlani, Lab on a Chip, 2012, 12, 515-45.
72. R. J. Cornish, Proceedings of the Royal Society of London, Ser. A, 1928, 120, 691-700.
73. T. Gervais, J. El-Ali, A. Günther, and K. F. Jensen, Lab on a Chip, 2006, 6, 500-7.
74. B. S. Hardy, K. Uechi, J. Zhen, and H. Pirouz Kavehpour, Lab on a Chip, 2009, 9, 935-8.
75. K. W. Oh, K. Lee, B. Ahn, and E. P. Furlani, *Lab on a Chip,* 2012, 12, 515-45.

The invention claimed is:

1. A fluid processing apparatus configured for separating particles from a fluid flowing through the apparatus, the apparatus comprising:
   a fluid inlet configured to receive a fluid containing particles;
   a main fluid channel extending from said fluid inlet and arranged in a spiral configuration and configured to cause differential migration of particles within the fluid flowing through said main fluid channel into unique equilibrium positions within said main channel according to a size of the particle thereby forming one or more particle streams and a particle-free region within the fluid flowing through said main channel;
   one or more outlets in fluid communication with said main fluid channel and configured to receive the particles from the one or more particle streams flowing from said main fluid channel; and
   one or more secondary channels extending from said main fluid channel along a length of said main fluid channel between the fluid inlet and the one or more outlets and configured to draw at least a portion of the fluid from the particle-free region within said main channel to increase the concentration of particles within the remaining fluid flowing through said main channel, wherein the main channel has a non-uniform geometry, wherein the geometry of the main channel is changed following a secondary channel to compensate for fluid removal via the secondary channel.

2. The fluid processing apparatus of claim 1, wherein the one or more particles sizes are in a range of 4.8 μm to 15 μm.

3. The fluid processing apparatus of claim 1, wherein the secondary channels are configured to draw a portion of the fluid of the particle-free region from said main channel to reduce the volume of fluid flowing through said main channel by about 10-95%.

4. The fluid processing apparatus of claim 1, wherein the particles are selected from the group consisting of DNA molecules, viruses, bacteria, fungi, cancer cells, white blood cells, and neutrophils.

5. The fluid processing apparatus of claim 1, wherein the fluid flowing through the apparatus comprises a sample and the particles comprise more than one component of interest within the sample, and wherein
   the fluid inlet is configured to receive the sample;
   the main fluid channel is configured so that the components of interest are focused into more than one component stream according to the size of the components, thereby forming a component-free region within the fluid flowing through said main channel;
   the apparatus includes more than one outlet in fluid communication with said main fluid channel and configured to receive the components of interest from the component streams flowing from said main fluid channel to filter each of the components of interest from the sample; and
   the one or more secondary channels are configured to draw at least a portion of the fluid from the component-free region within said main channel to increase the concentration of components of interest within the remaining fluid flowing through said main channel.

6. The fluid processing apparatus of claim 1, wherein said fluid inlet is located at an inner end portion of the spiral configuration of said main channel, the one or more outlets are located at an outer end portion of the spiral configuration of the main channel, and said one or more secondary channels extend radially outwardly from an outer loop of the spiral configuration of said main channel.

7. The fluid processing apparatus of claim 1, wherein said main channel has a non-uniform width varying along the length of said main channel.

8. The fluid processing apparatus of claim 7, comprising at least two secondary channels, and wherein the width of said main channel is substantially constant between each two neighboring secondary channels.

9. The fluid processing apparatus of claim 1, wherein the geometry of said main channel is changed following a secondary channel to compensate for fluid removal via the secondary channel.

10. The fluid processing apparatus of claim 9, wherein the geometry of said main channel is changed following a secondary channel to maintain a constant or substantially constant flow velocity within said main channel before and after the secondary channel.

11. The fluid processing apparatus of claim 10, wherein the geometry of said main channel is changed by changing the width of the main channel, and the new width $w_{m,j}$ of the main channel following a $j^{th}$ secondary channel is determined by the formula:

$$w_{m,j-1} = x_{m,j-1} w_{m,j},$$

wherein $x_{m,j-1}$ is the fraction of fluid remaining in the main channel after fluid removal through the jth secondary channel, and $w_{m,j}$ is the width of the previous section of said main channel.

12. The fluid processing apparatus of claim 9, wherein the geometry of said main channel is changed following a secondary channel to maintain a constant or substantially constant Dean number, De, within said main channel before and after the secondary channel, wherein the Dean number, De, is given by the formula:

$$De = \frac{\rho U_f D_h}{\mu} \sqrt{\frac{D_h}{2R}}$$

wherein ρ is the density of the fluid, $U_f$ is average fluid velocity, μ is fluid dynamic viscosity, R is the radius of curvature of said main channel, and $D_h$ is a hydraulic diameter, and wherein the hydraulic diameter, $D_h$, is determined from:

$$D_h = \frac{2wh}{w+h},$$

wherein w is the width of said main channel and h is the height of said main channel.

13. The fluid processing apparatus of claim 9, wherein the geometry of said main channel is changed by changing the width of the main channel.

14. The fluid processing apparatus of claim 13, wherein a downstream corner of a junction between said main channel and said secondary channel is filleted to allow for a gradual change in the width of said main channel.

15. The fluid processing apparatus of claim 1, comprising between one and five outlets.

16. The fluid processing apparatus of claim 1, comprising between one and six secondary channels.

17. The fluid processing apparatus of claim 1, wherein each secondary channel extends from an outer edge of an outer-most ring of the spiral configuration of said main channel.

18. The fluid processing apparatus of claim 1, wherein each of said one or more secondary channels is configured to draw from 5 to 50% of the fluid flowing through said main channel.

19. The fluid processing apparatus of claim 1, wherein each secondary channel comprises a meander path.

20. The fluid processing apparatus of claim 1, wherein the apparatus is fabricated from polydimethylsiloxane.

21. The fluid processing apparatus of claim 1, wherein the apparatus is configured to accommodate a flow rate of between 100 µL/min and 1250 µL/min.

22. The fluid processing apparatus of claim 1, wherein the apparatus is configured to process fluid at a rate of 1 mL/min.

23. The fluid processing apparatus of claim 1, wherein the width of each secondary channel is set to draw a specified portion of the fluid of the particle-free region from said main channel according to the formula:

$$w \approx \frac{12\mu L}{h^3 R_H} + 0.63h$$

wherein w is the width of the secondary channel, h is the height of the secondary channel, L is the length of the secondary channel, µ is the dynamic viscosity of the fluid, and $R_H$ is the hydraulic resistance of the secondary channel.

24. The fluid processing apparatus of claim 1, wherein the fluid resistance of a secondary channel required to draw fluid from the main channel at a specified rate satisfies the relationship:

$$R_{s,j} = r_{Q,j}\left(R_{m,j} + \frac{R_{s,j-1}}{1+r_{Q,j-1}}\right)$$

where $R_{s,j}$ is the fluid resistance of the $j^{th}$ secondary channel at the $j^{th}$ node where the $j^{th}$ secondary channel connects to said main channel, $R_{m,j}$ is the fluid resistance of said main channel at the $j^{th}$ node, $R_{s,j-1}$ is the fluid resistance of the secondary channel at a previous node j–1, and $r_{Q,j-1}$ is the volumetric flow ratio of flow within said main channel ($Q_{m,j}$) to flow within the secondary channel ($Q_{s,j}$) at the $j^{th}$ node.

25. The fluid processing apparatus of claim 1, wherein the spiral configuration of said main channel comprises a 6 or 7-loop spiral.

26. The fluid processing apparatus of claim 1, wherein said main channel comprises a width of about 250 µm and a height of about 50 µm.

27. The fluid processing apparatus of claim 25, comprising a single inlet, a single secondary channel, and a bifurcating outlet, and wherein said spiral main channel has a 250 µm gap between successive loops.

28. The fluid processing apparatus of claim 25, wherein the spiral configuration is an Archimedean spiral.

29. The fluid processing apparatus of claim 26, wherein the width of the secondary channel is between 40 and 250 µm.

30. The fluid processing apparatus of claim 26, wherein the length of the secondary channel is about 19 mm.

31. The fluid processing apparatus of claim 1, wherein each secondary channel comprises a width of about 35 µm, a height of about 50 µm, and a length of about 19 mm.

* * * * *